(12) United States Patent
Vali et al.

(10) Patent No.: US 11,478,444 B2
(45) Date of Patent: Oct. 25, 2022

(54) USE OF SCIENTIFICALLY MATCHED PLANT SUPPLEMENTS COMBINED WITH ANTINEOPLASTIC COMPOUNDS FOR THE TREATMENT OF HEMATOLOGICAL MALIGNANCIES

(71) Applicant: Brio Ventures, LLC, Gainesville, FL (US)

(72) Inventors: Shireen Vali, Irvine, CA (US); Taher Abbasi, Irvine, CA (US); Tomas Stopka, Dolní Břežany (CZ); Lubomir Minarik, Prague (CZ); Neeraj Kumar Singh, Bengaluru (IN); Shahabuddin Usmani, Bengaluru (IN); Saumya Radhakrishnan, Sittingbourne (GB); Huzaifa Sikora, Bengaluru (IN); Robinson Vidva, Bengaluru (IN); Kristyna Pimkova, Lednice (CZ)

(73) Assignee: Brio Ventures, Gainesville, FL (US)

( * ) Notice: Subject to any disclaimer, the term of this patent is extended or adjusted under 35 U.S.C. 154(b) by 118 days.

(21) Appl. No.: 17/168,644

(22) Filed: Feb. 5, 2021

(65) Prior Publication Data
US 2021/0244703 A1 Aug. 12, 2021

Related U.S. Application Data

(60) Provisional application No. 62/971,237, filed on Feb. 7, 2020.

(51) Int. Cl.
| | |
|---|---|
| *A61K 31/26* | (2006.01) |
| *A61P 35/02* | (2006.01) |
| *A61K 9/00* | (2006.01) |
| *A61K 31/05* | (2006.01) |
| *A61K 31/12* | (2006.01) |
| *A61K 31/706* | (2006.01) |
| *A61K 45/06* | (2006.01) |

(52) U.S. Cl.
CPC ............ *A61K 31/26* (2013.01); *A61K 9/0053* (2013.01); *A61K 31/05* (2013.01); *A61K 31/12* (2013.01); *A61K 31/706* (2013.01); *A61K 45/06* (2013.01); *A61P 35/02* (2018.01)

(58) Field of Classification Search
CPC ........ A61K 31/26; A61K 31/05; A61K 31/12; A61K 36/9066; A61P 35/02
See application file for complete search history.

(56) References Cited

U.S. PATENT DOCUMENTS

2020/0206246 A1\* 7/2020 Harding ............... A61K 31/585

\* cited by examiner

*Primary Examiner* — Sahar Javanmard
(74) *Attorney, Agent, or Firm* — Brio Ventures

(57) ABSTRACT

The present disclosure relates to the field of combination therapy for treatment of hematological malignancy selected from myelodysplastic syndrome (MDS) and acute myeloid leukemia (AML). The disclosure provides a combination therapy comprising plant based compounds and hypomethylating agent (HMA). Particularly, the disclosure provides a combination of: a) a therapeutically effective amount of a combination comprising sulforaphane, resveratrol and curcumin; and b) a therapeutically effective amount of HMA selected from azacitidine (AZA), decitabine (DEC) and a combination thereof, for treating MDS or AML. Said combination provides an enhanced/synergistic effect in the treatment of MDS or AML along with decreasing or overcoming resistance to HMA (azacitidine or decitabine). Methods for decreasing or overcoming resistance to HMA (azacitidine or decitabine), corresponding use of the above described combination and a kit comprising said combination are also provided.

20 Claims, 16 Drawing Sheets

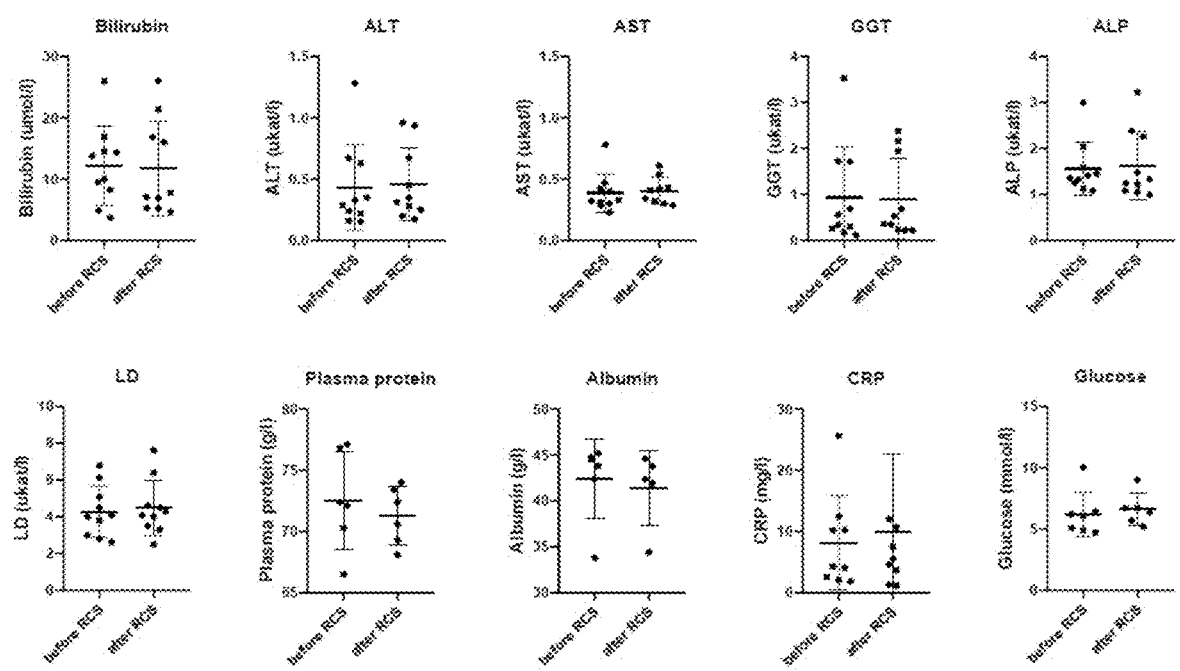
FIGURE 18 (contd.)

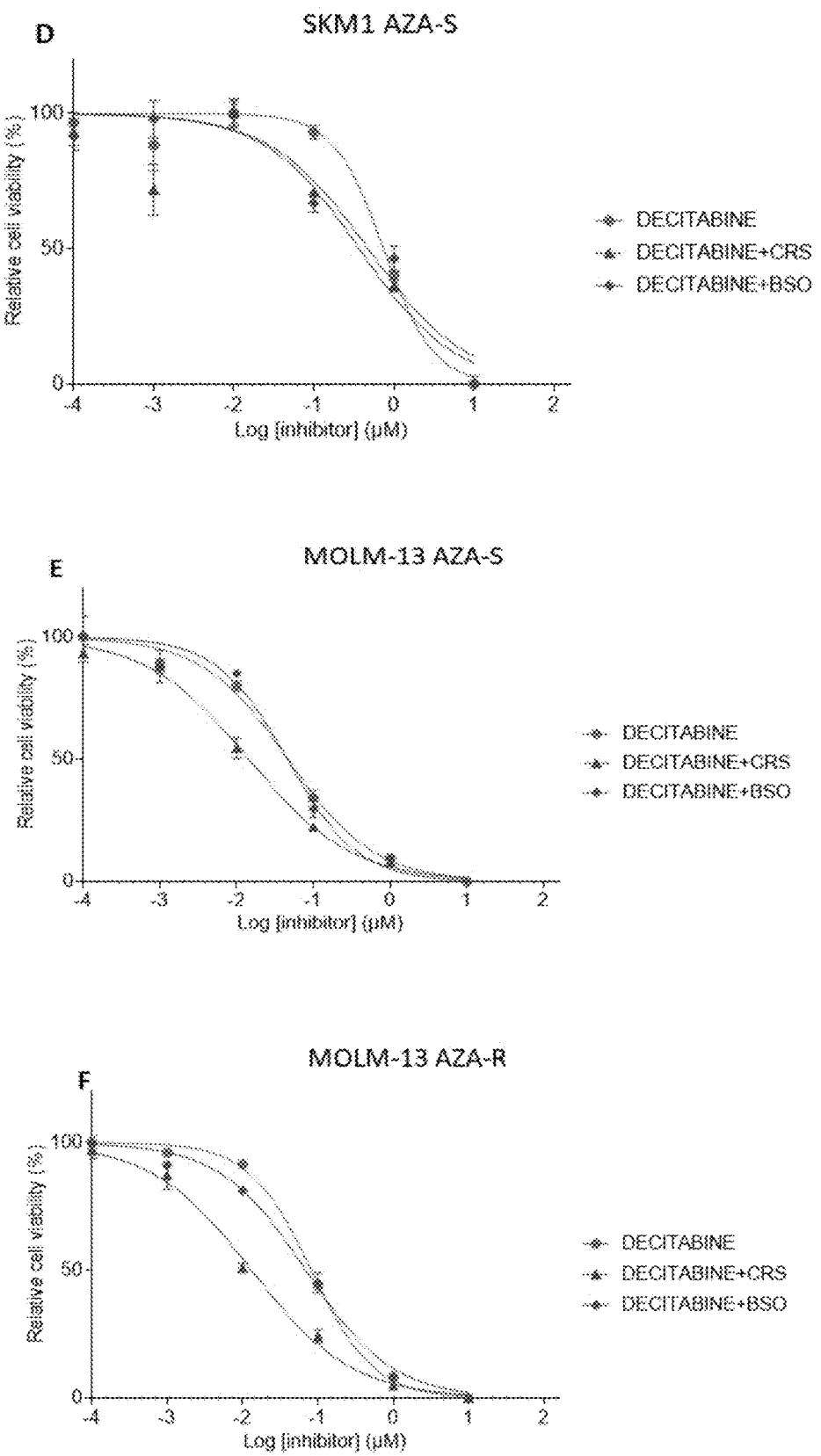
FIGURE 20 (contd.)

USE OF SCIENTIFICALLY MATCHED PLANT SUPPLEMENTS COMBINED WITH ANTINEOPLASTIC COMPOUNDS FOR THE TREATMENT OF HEMATOLOGICAL MALIGNANCIES

RELATED APPLICATIONS

This patent application claims the benefit of U.S. Provisional Application Ser. No. 62/971,237 entitled "USE OF SCIENTIFICALLY MATCHED PLANT SUPPLEMENTS COMBINED WITH ANTINEOPLASTIC COMPOUNDS FOR THE TREATMENT OF HEMATOLOGICAL MALIGNANCIES" filed on Feb. 7, 2020. The entire contents of the above-cited provisional application are hereby incorporated by reference in their entirety for all purposes.

TECHNICAL FIELD

The present disclosure relates to the field of a combination therapy for treatment of hematological malignancies. In particular, the disclosure relates to a combination therapy comprising plant based compounds and hypomethylating agent (HMA).

BACKGROUND OF THE DISCLOSURE

Hematological malignancies such as myelodysplastic syndrome (MDS) and Acute Myeloid Leukemia (AML) are myeloid blood diseases arising from bone marrow stem cells. MDS is a set of clonal hematopoietic differentiation disorders that lead to cytopenia. AML is characterized by the rapid proliferation of three lineage bone marrow precursors: the granulocyte lineage, the erythrocyte lineage and the megakaryocyte lineage, which cause the accumulation of immature cells in blood and bone marrow, resulting in abnormal hematopoiesis.

Although hypomethylating agents (HMA) such as azacitidine (AZA) or decitabine (DEC) are approved standard of care in MDS, the response rate does not exceed 50%. There is a significant percentage of MDS patients that progress to AML either due to loss of response to during the course of treatment (relapse) or refractoriness. The response of azacitidine is observed only in one third of de novo AML patients while two-thirds are refractory (insensitive) to the treatment. The mechanism of sensitivity or resistance for hypomethylating agents such as azacitidine is not fully understood baring few reported genomic aberrations in support of either of the responses. Particularly, understanding hypomethylating agent (HMA) resistance is quite complex as the resistant clones take over to divide in an uncontrolled and undifferentiated manner. There is no one unique reason for resistance towards these hypomethylating agents as they are of varied nature depending on the genomic make-up of patients or the in vitro models. Hence, the management of MDS or AML patients becomes very difficult and is highly unpredictable, especially the patients who gain resistance to hypomethylating agents such as azacitidine or decitabine.

Hence, there is an unmet need of new/alternative approaches for better management or treatment of hematological malignancies and at the same time approaches to deal with resistance to standard chemotherapeutic drugs such as hypomethylating agents (azacitidine and decitabine).

SUMMARY OF THE DISCLOSURE

The present disclosure relates to a method for decreasing resistance to a hypomethylating agent (HMA) caused by treatment of hematological malignancy in a subject in need thereof, the method comprising administering a therapeutically effective amount of a combination comprising sulforaphane, resveratrol and curcumin to the subject. In some embodiments, the hypomethylating agent (HMA) is azacitidine (AZA), or decitabine (DEC), or a combination thereof. In some embodiments, the hypomethylating agent (HMA) is azacitidine (AZA). In some embodiments, the hematological malignancy is myelodysplastic syndrome (MDS) or acute myeloid leukemia (AML). In some embodiments, the subject has already been administered or is undergoing treatment with a therapeutically effective amount of the hypomethylating agent (HMA). In some embodiments, decreasing resistance according to the method comprises improving sensitivity of the subject to the hypomethylating agent (HMA) during treatment of the hematological malignancy.

The present disclosure also provides a method of treating a hematological malignancy selected from myelodysplastic syndrome (MDS) and acute myeloid leukemia (AML) in a subject in need thereof, the method comprising administering:
a) a therapeutically effective amount of a combination comprising sulforaphane, resveratrol and curcumin; and
b) a therapeutically effective amount of hypomethylating agent (HMA) selected from azacitidine (AZA), decitabine (DEC) and a combination thereof, to the subject. In some embodiments, the method has an enhanced therapeutic effect in the treatment of the hematological malignancy compared to the effect of hypomethylating agent (HMA) when administered alone. In some embodiments, the method improves sensitivity of the subject to the hypomethylating agent (HMA) during treatment of the hematological malignancy.

The present disclosure further provides pharmaceutical kit and use of the combination of the present disclosure viz. a) a therapeutically effective amount of a combination comprising sulforaphane, resveratrol and curcumin; and b) a therapeutically effective amount of hypomethylating agent (HMA) selected from azacitidine (AZA), decitabine (DEC) and a combination thereof, for treating hematological malignancy—myelodysplastic syndrome (MDS) or acute myeloid leukemia (AML).

BRIEF DESCRIPTION OF THE ACCOMPANYING FIGURES

Figure 3:
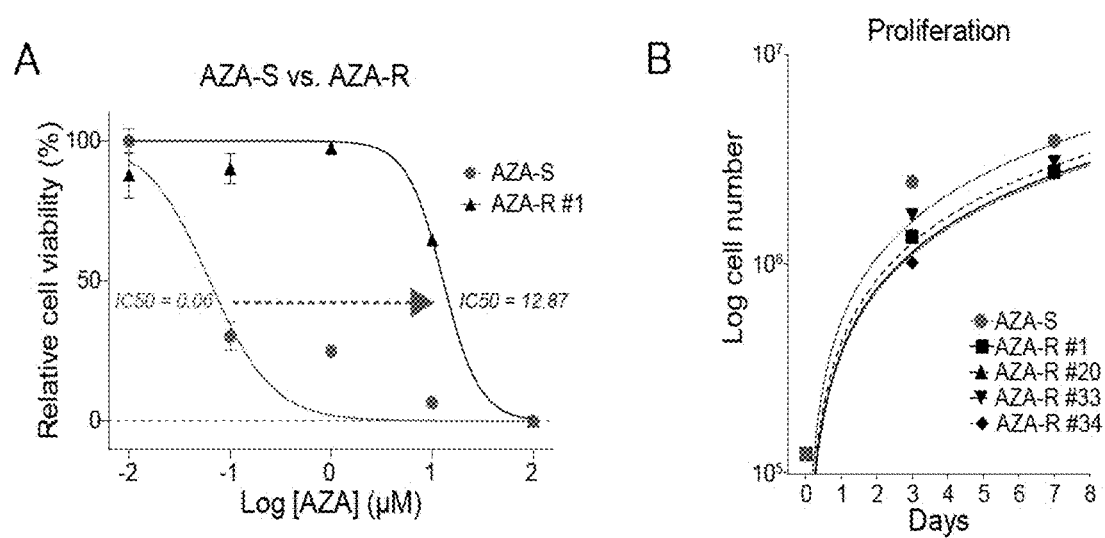

FIG. 3 shows cell viability and proliferation results of OCI-M2 AZA-S and OCI-M2 AZA-R cells. Legend: [AZA—Azacitidine, S—Sensitive, R—Resistant]. AZA-R #1, AZA-R #20, AZA-R #33 and AZA-R #34 are different Azacitidine-resistant (AZA-R) clones that were selected based on the screening using Azacitidine-sensitive (AZA-S) cells treated by high dose of AZA.

Figure 4:
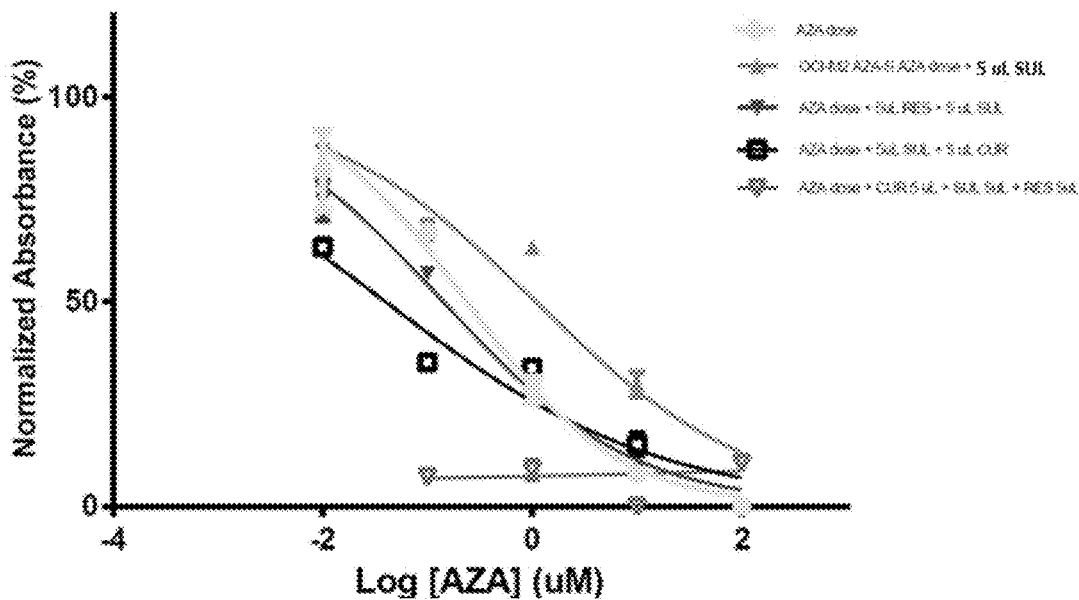

FIG. 4 shows the effect of different combinations of sulforaphane, resveratrol and curcumin on OCI-M2 AZA-S [sensitive] cells with addition of AZA. Legend: [AZA—Azacitidine, SUL—Sulforaphane, RES—Resveratrol, CUR—Curcumin]

Figure 5:
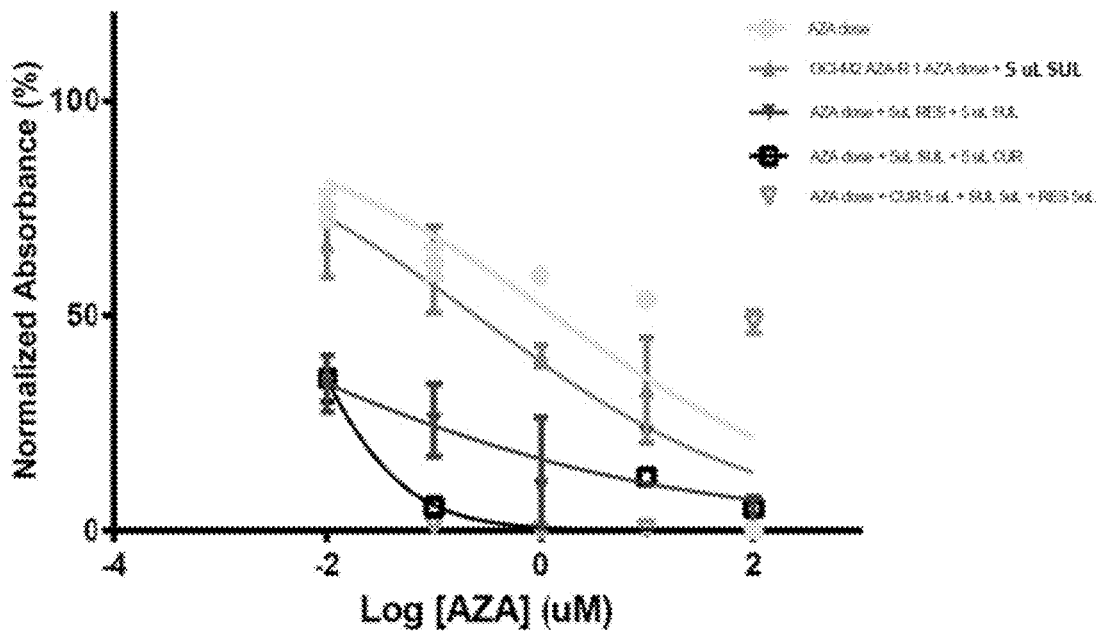

FIG. 5 shows the effect of different combinations of sulforaphane, resveratrol and curcumin on OCI-M2 AZA-R #1 [Resistant] cells with addition of AZA. Legend: [AZA—Azacitidine, SUL—Sulforaphane, RES—Resveratrol, CUR—Curcumin]

Figure 6:
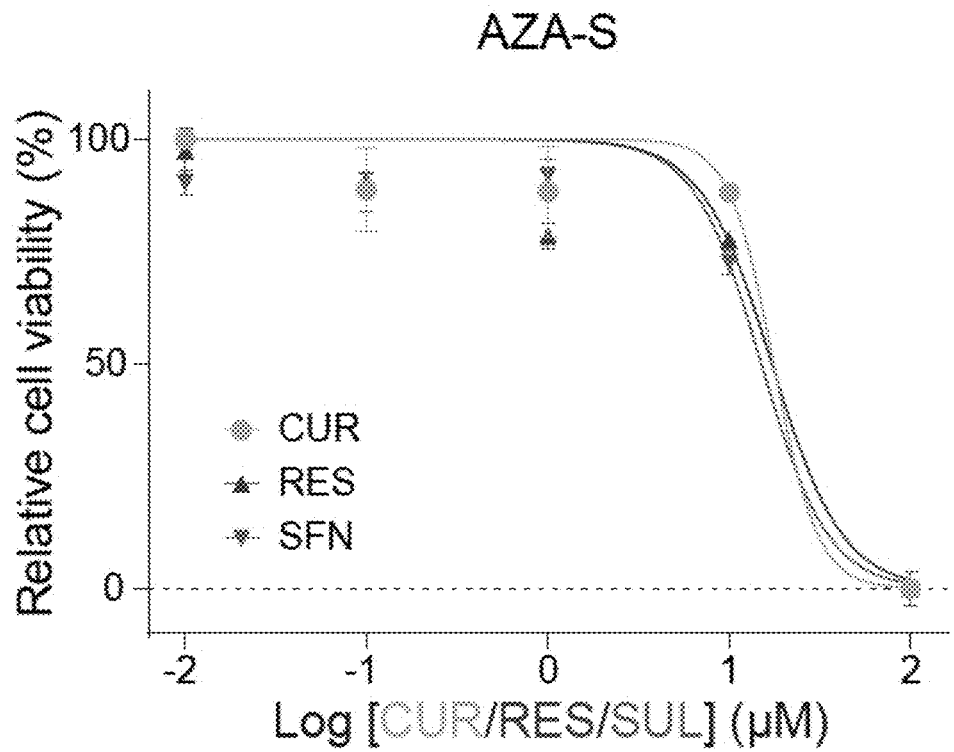

FIG. 6 shows the effect of sulforaphane, resveratrol and curcumin treatment on OCI-M2 AZA-S cells across a large concentration gradient. Legend: [AZA-S—Azacitidine Sensitive, SUL—Sulforaphane, RES—Resveratrol, CUR—Curcumin]

Figure 7:
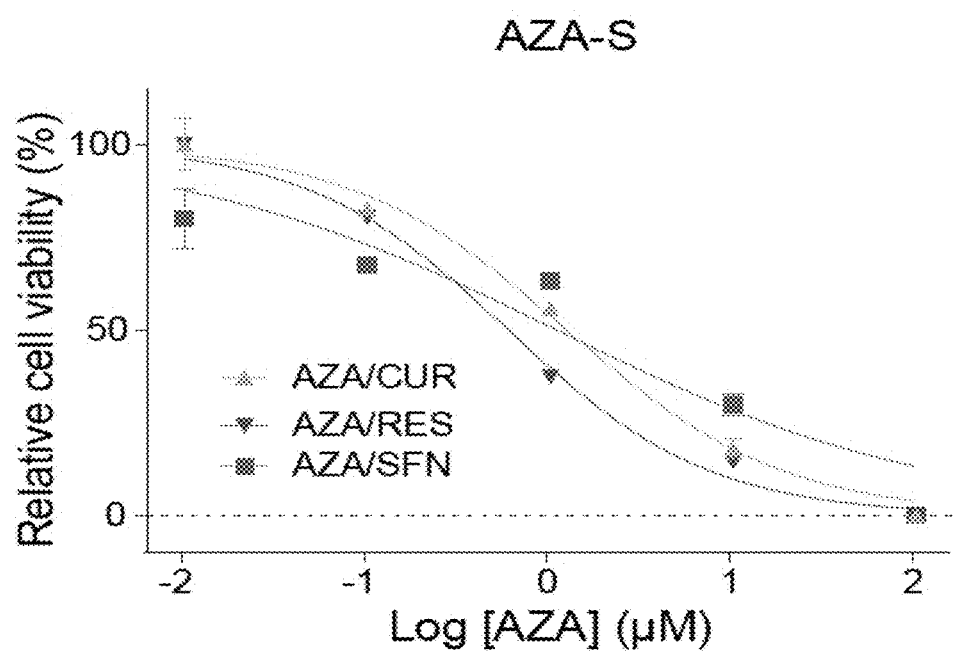

FIG. 7 shows the effect of sulforaphane, resveratrol and curcumin treatment on OCI-M2 AZA-S cells followed by addition of AZA at different concentrations. Legend: [AZA-S—Azacitidine Sensitive, SFN—Sulforaphane, RES—Resveratrol, CUR—Curcumin]

Figure 8:
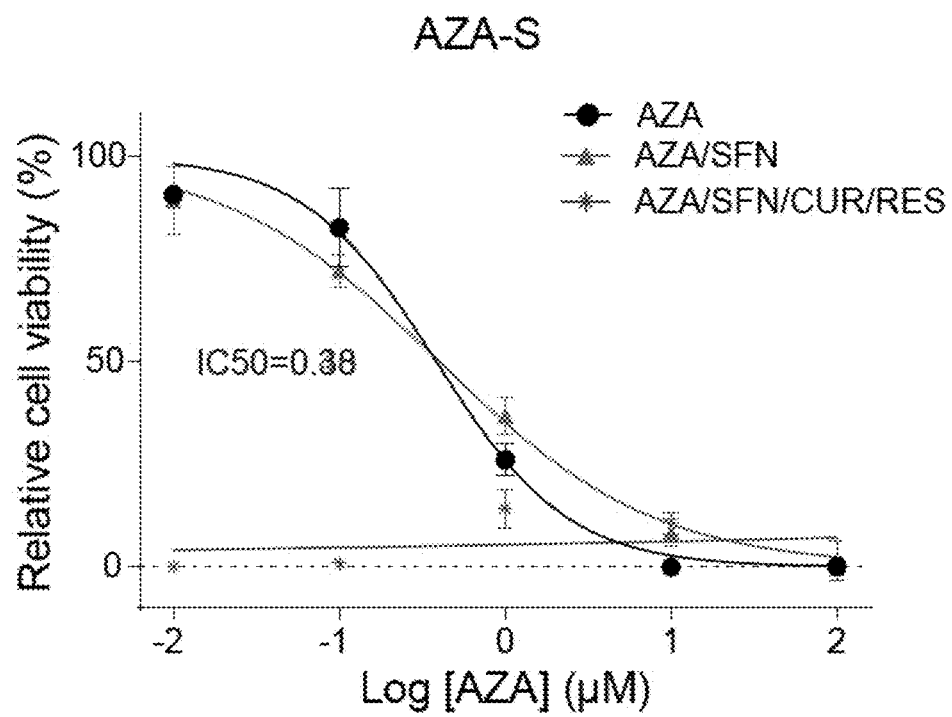

FIG. 8 shows the effect of sulforaphane vs. the combination of sulforaphane+resveratrol+curcumin treatment on OCI-M2 AZA-S [Sensitive] cells followed by addition of AZA at different concentrations. Legend: [AZA—Azacitidine, SFN—Sulforaphane, RES—Resveratrol, CUR—Curcumin]. $IC_{50}$ values: AZA-S cells+AZA=0.38 uM; AZA-S cells+AZA/SFN=0.40 uM; and AZA-S cells+AZA/SFN/CUR/RES<0.01 uM.

Figure 9:
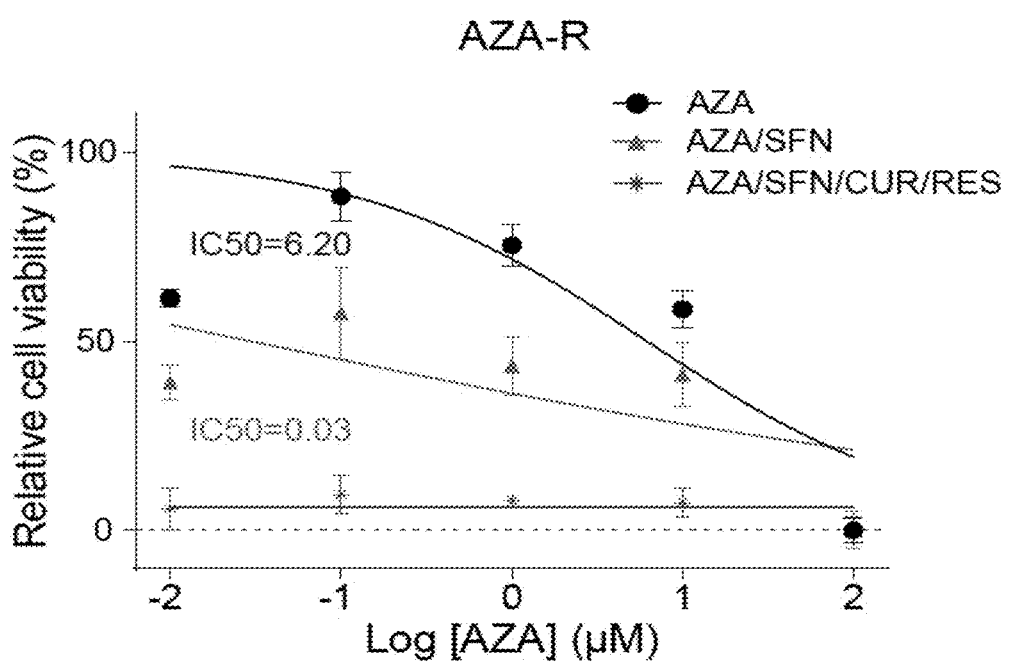

FIG. 9 shows the effect of sulforaphane vs. the combination of sulforaphane+resveratrol+curcumin treatment on OCI-M2 AZA-R [Resistant] cells followed by addition of AZA at different concentrations. Legend: [AZA—Azacitidine, SFN—Sulforaphane, RES—Resveratrol, CUR—Curcumin]. IC50 values: AZA-R cells+AZA=6.20 uM; AZA-R cells+AZA/SFN=0.03 uM; and AZA-R cells+AZA/SFN/CUR/RES<0.01 uM.

Figure 10:
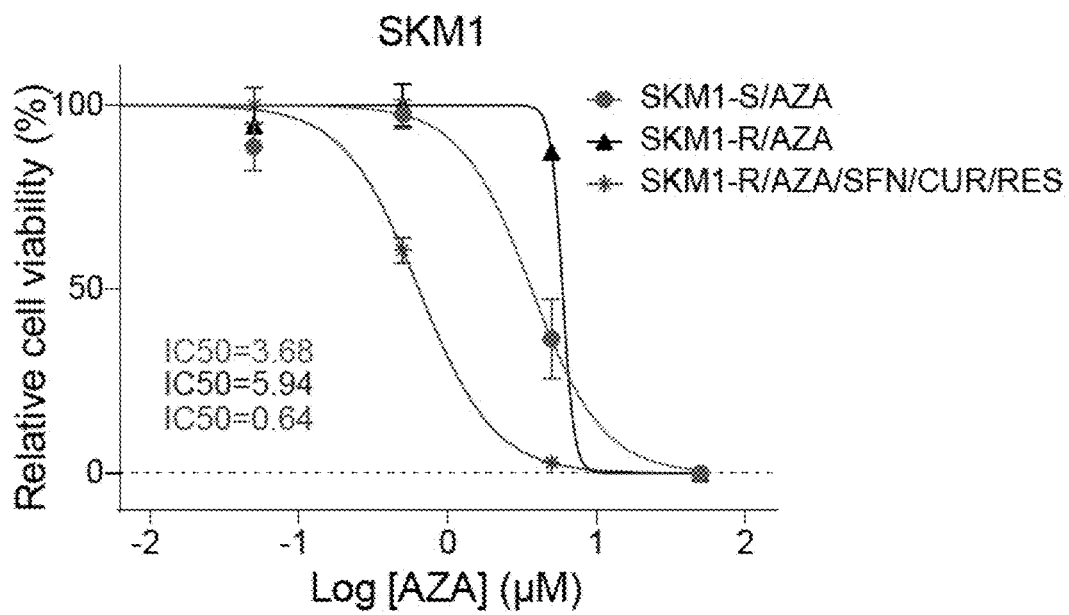

FIG. 10 shows the effect of combination of sulforaphane+resveratrol+curcumin treatment on SKM1-R [Resistant] cells followed by addition of AZA at different concentrations. Legend: [AZA—Azacitidine, SFN—Sulforaphane, RES—Resveratrol, CUR—Curcumin]

Figure 11:
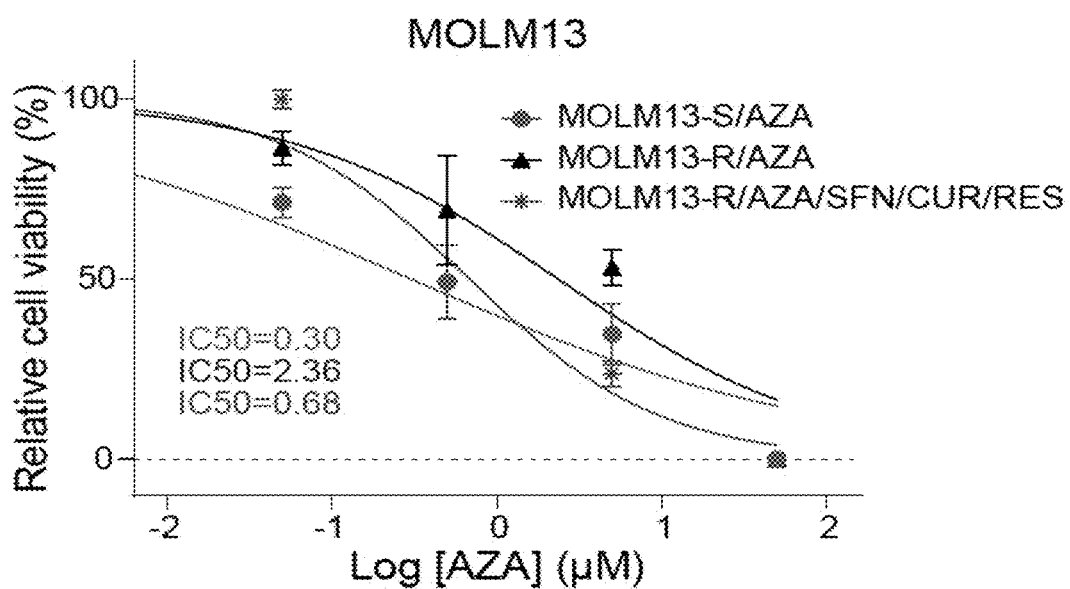

FIG. 11 shows the effect of combination of sulforaphane+resveratrol+curcumin treatment on MOLM13-R [Resistant] cells followed by addition of AZA at different concentrations. Legend: [AZA—Azacitidine, SFN—Sulforaphane, RES—Resveratrol, CUR—Curcumin]

Figure 12:
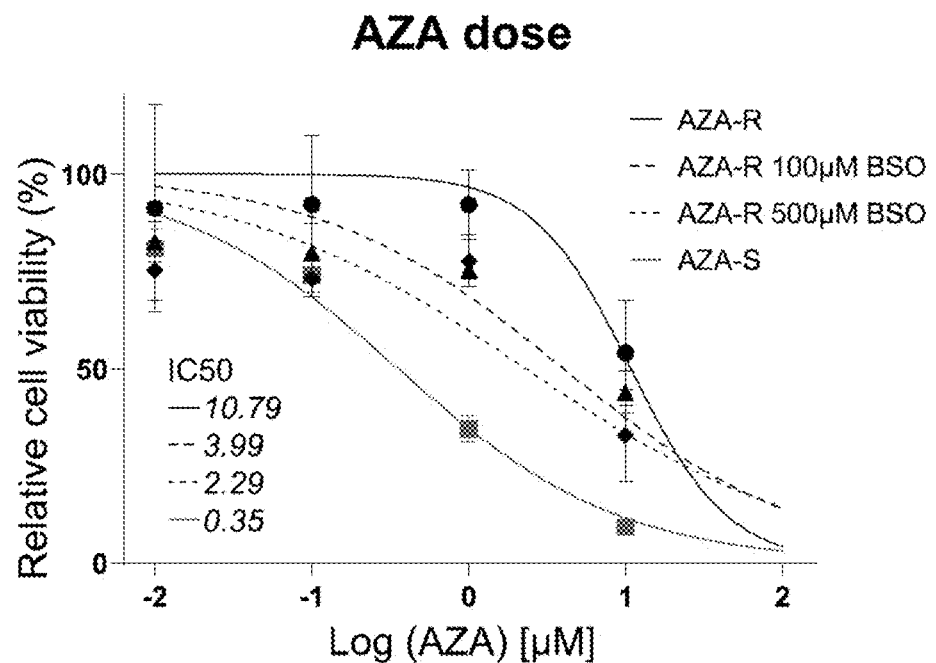

FIG. 12 shows the effect of DL-buthionine-sulfoximine (BSO) [GSH Inhibitor] treatment on cytotoxicity of AZA in a dose-dependent manner. Legend: [AZA—Azacitidine, BSO—DL-buthionine-sulfoximine]

Figure 13:
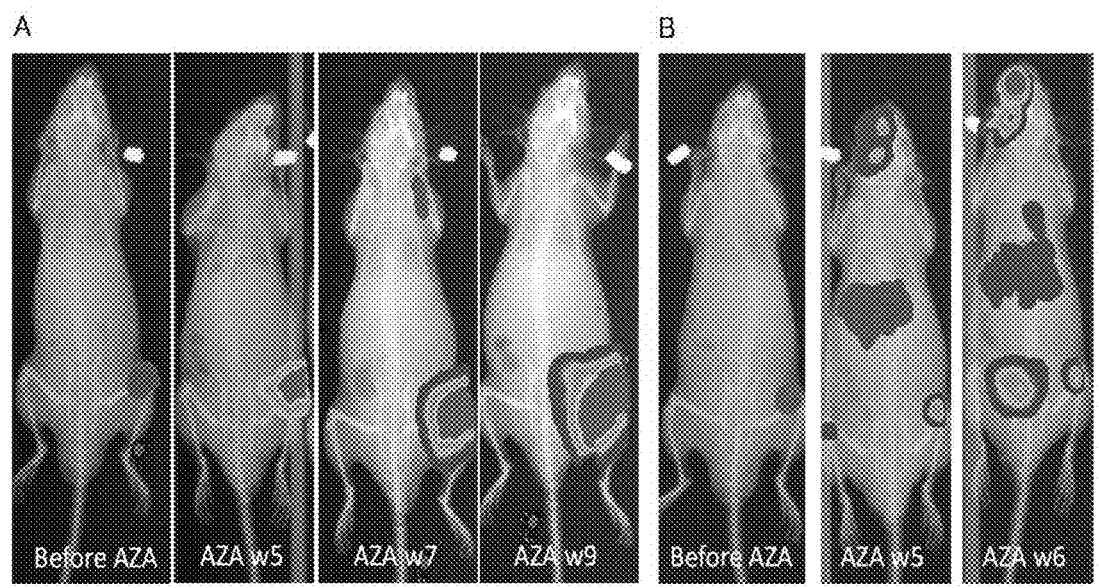

FIG. 13 shows in vivo imaging of (A) AZA-S and (B) AZA-R cell lines transfected Cell-line Derived Xenograft (CDX) mice models.

Figure 14:
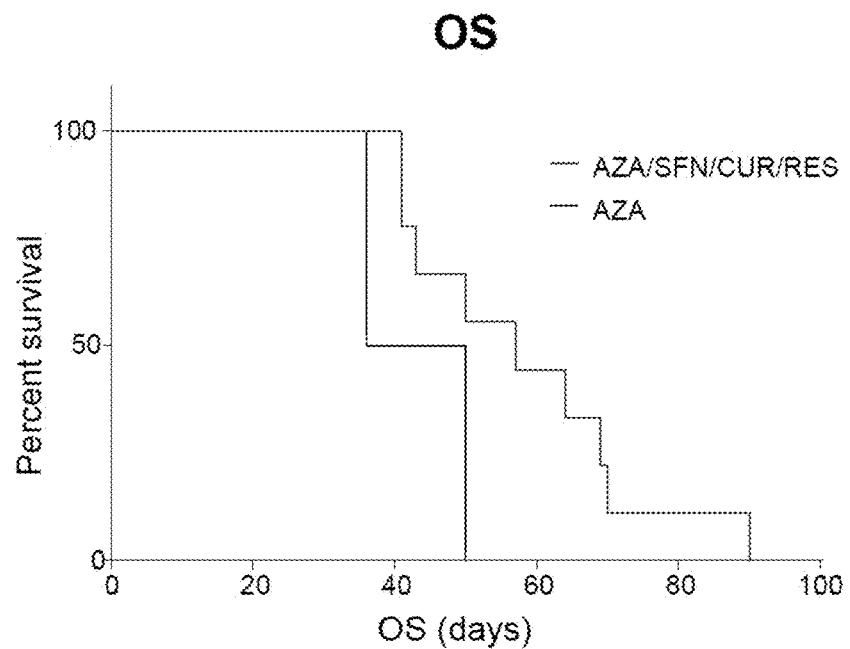

FIG. 14 shows OS (Overall Survival) curve for mice xeno-transplanted with AZA-R cells treated with AZA compared to mice xeno-transplanted with AZA-R cells treated with the combination of SFN+RES+CUR and AZA [43 vs. 57 days, p value=0.038].

Figure 15:
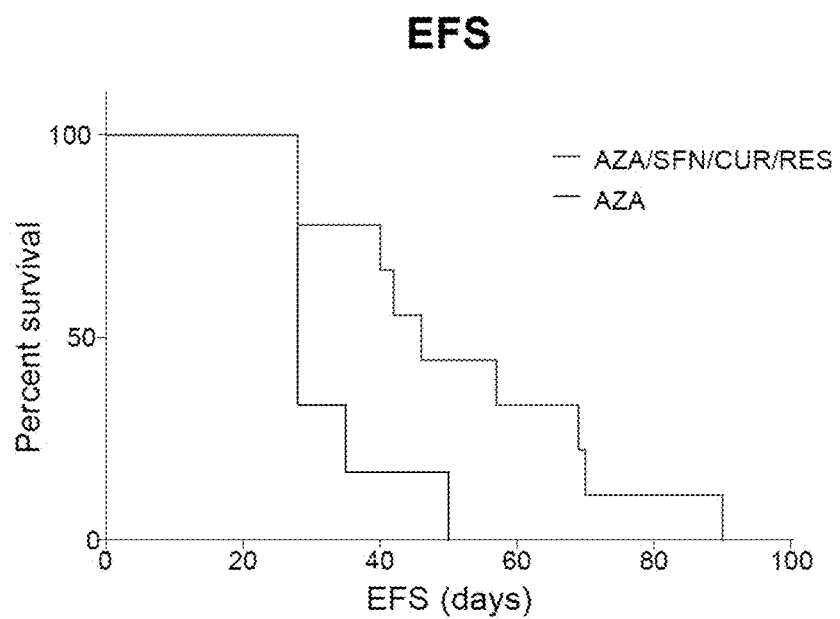

FIG. 15 shows EFS (Event Free Survival) curve for mice xeno-transplanted with AZA-R cells treated with AZA compared to mice xeno-transplanted with AZA-R cells treated with the combination of SFN+RES+CUR and AZA (28 vs. 46 days, p value=0.032).

Figure 16:

FIG. 16 shows clinical study results in high-risk MDS/AML patients who undertook administration of Sulforaphane, Resveratrol and Curcumin along with standard chemotherapy (azacitidine). Figure Legend: Swimmers plot of 10 patients diagnosed with HR-MDS (Higher-Risk Myelodysplastic Syndrome) or MDS/AML (Myelodysplastic syndrome and acute myeloid leukemia) treated with AZA (green) and with the combination of oral supplements RCS—Resveratrol, Curcumin and Sulforaphane represented as Addone (yellow). Other therapies (blue and violet) and response (grey or red circle) are also indicated. Clinical data are shown within a table on the right. X axis indicates days.

Figure 17:
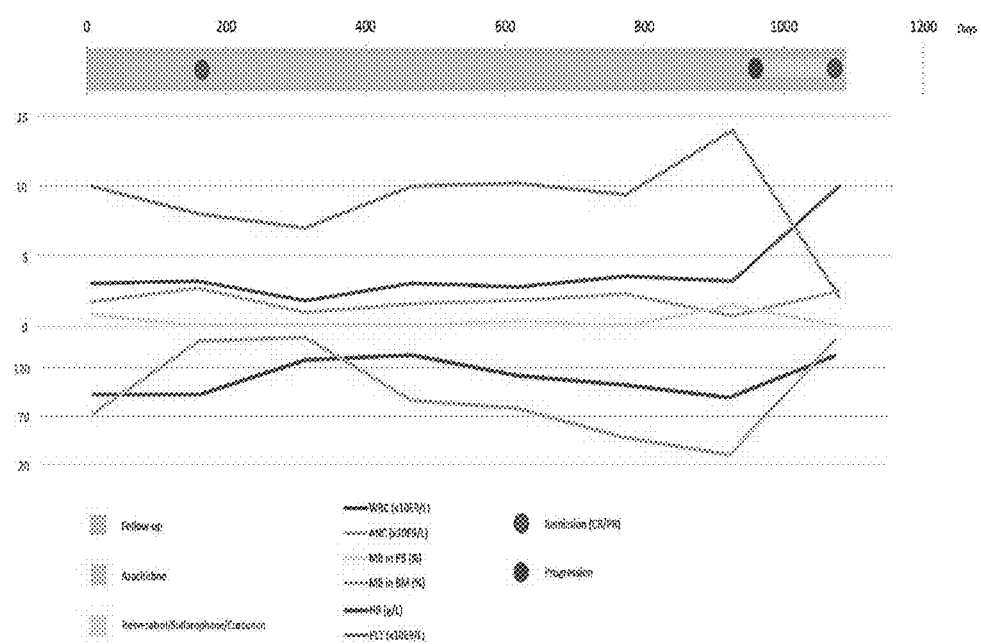

FIG. 17 shows clinical study of MDS/AML patient CRS004 indicating reversal of azacitidine resistance and improvement in the treatment of MDS/AML when administered with Sulforaphane, Resveratrol and Curcumin along with standard chemotherapy (azacitidine).

Case Study Details/Timelines—GA028 (Arm GA)/CRS004:
  January 2018: Dg. t-MDS, EB2 (IPSS-R very high risk—complex karyotype and TP53mut p.Val173Leu)
  March 2018: started AZA therapy, achieved partial remission (PR) which lasted for approximately 2 years
  October 2020: progression back to EB2 stage. At this point, he started Sulforaphane, Resveratrol and Curcumin supplementation along with standard AZA therapy
  January 2021: achieving complete remission 1 (CR1)

Figure 18:
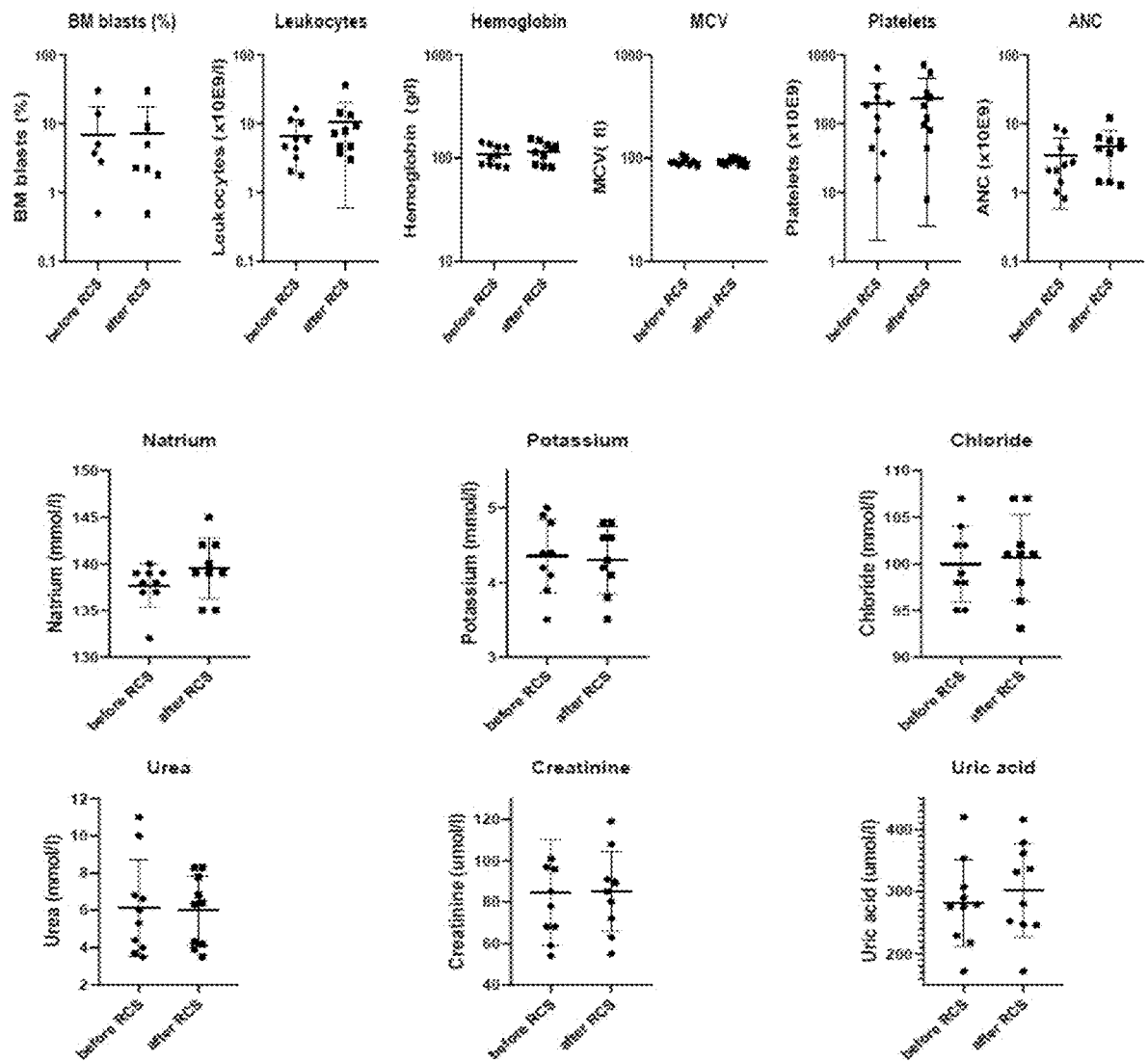

FIG. 18 shows test results of whole blood cell levels, selected set of biochemical tests and tests results to identify myelo, hepato or renal toxicity and any signs of tumor lysis syndrome.

Figure 19:
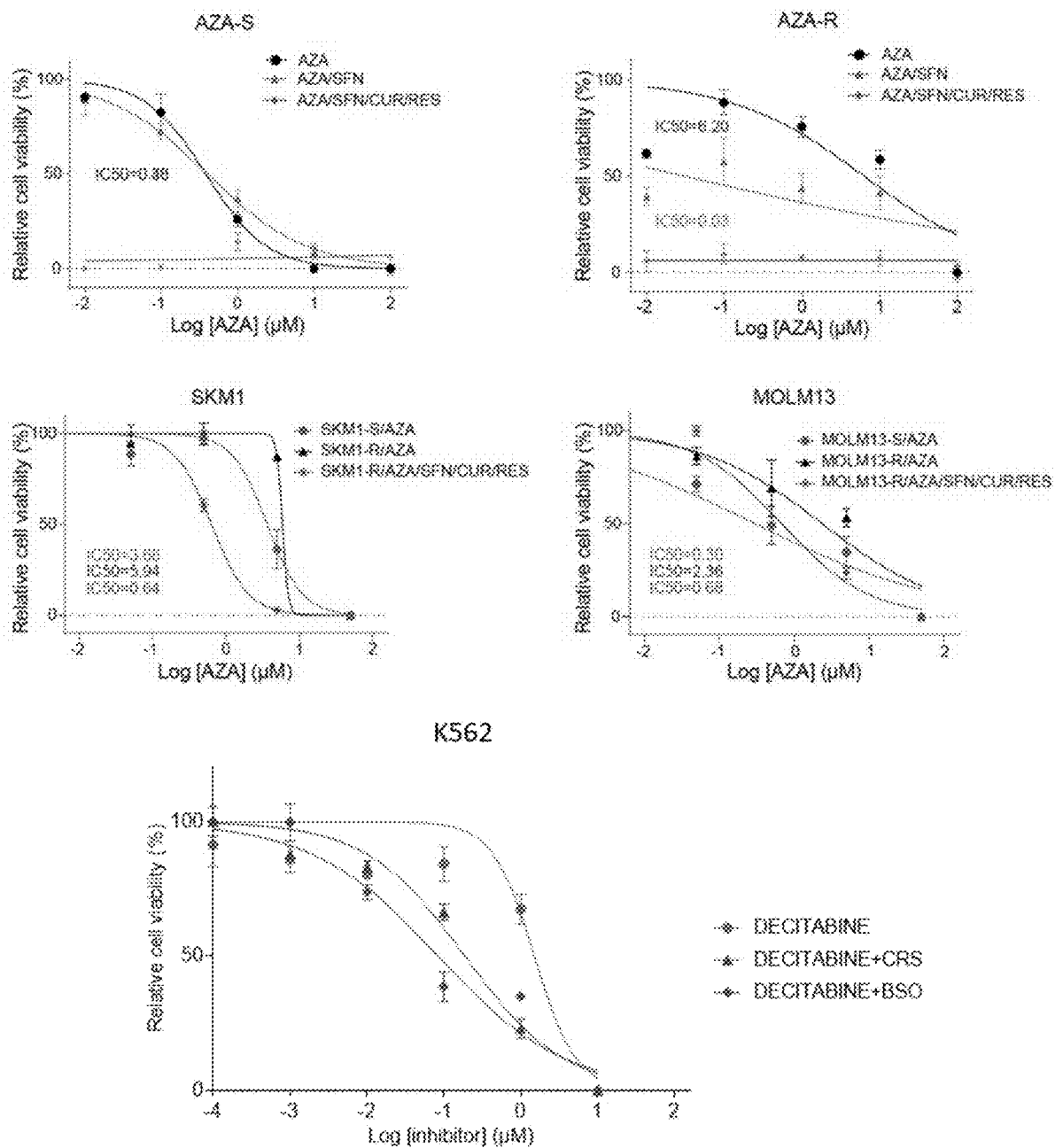

FIG. 19 shows additional cytotoxic effect based on certain genomic aberrations in different cancer cell lines.

Figure 20:
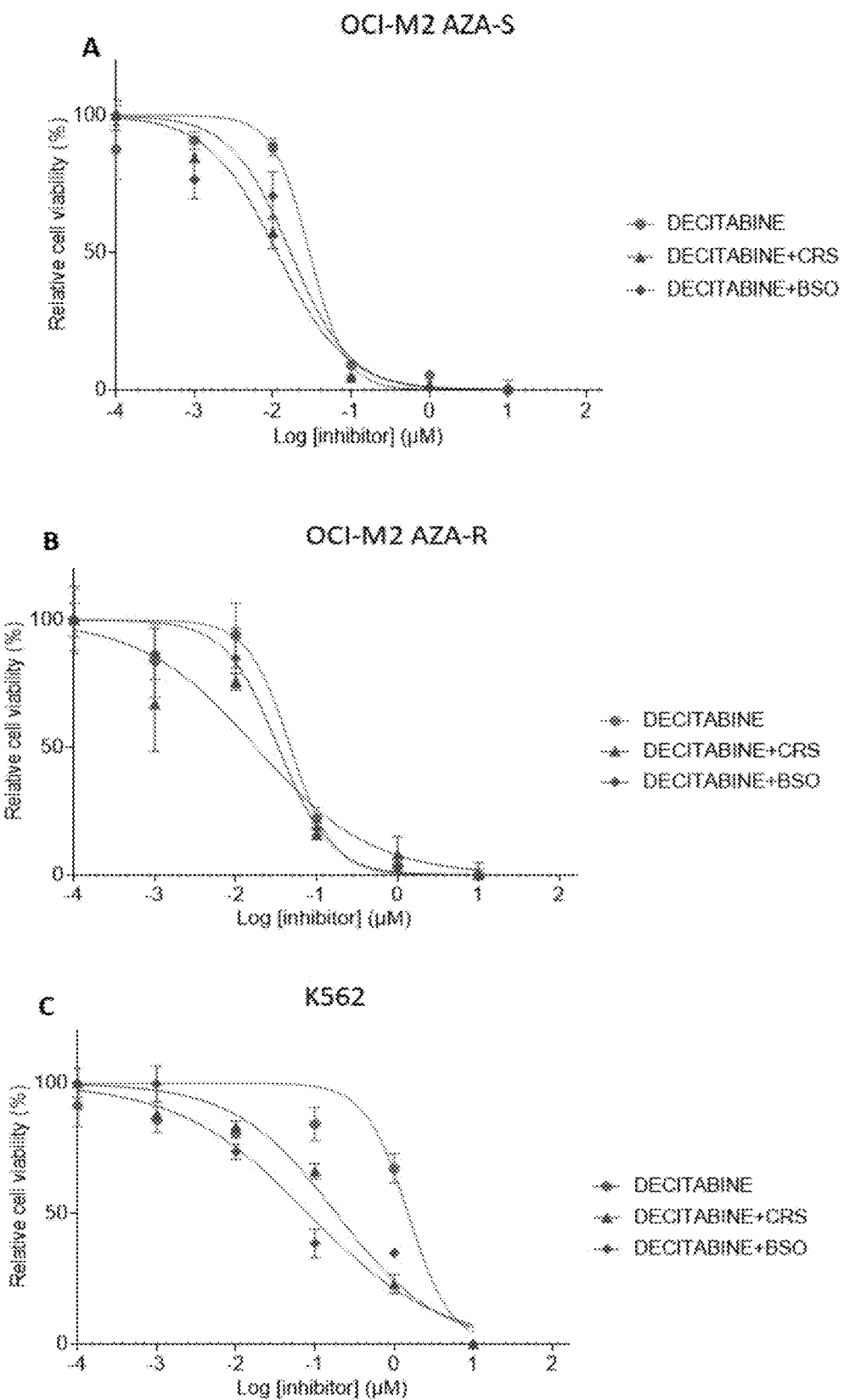

FIG. 20 illustrates the effect of CRS (curcumin, resveratrol and sulforaphane) along with decitabine in different cell lines.

DETAILED DESCRIPTION OF THE DISCLOSURE

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The use of the expression "at least" or "at least one" suggests the use of one or more elements or ingredients or quantities, as the use may be in the embodiment of the disclosure to achieve one or more of the desired objects or results. Throughout this specification, the word "comprise", or variations such as "comprises" or "comprising" or "containing" or "has" or "having", or "including but not limited to" wherever used, will be understood to imply the inclusion of a stated element, integer or step, or group of elements, integers or steps, but not the exclusion of any other element, integer or step, or group of elements, integers or steps. Further, the use of the expression "essentially consisting of" or "consisting essentially of" will be understood to imply the inclusion of the stated element, integer or step, or group of elements, integers or steps, along with those additional element(s) that do not materially affect the basic and novel characteristic(s) of the present invention.

Reference throughout this specification to "one embodiment" or "an embodiment" or "some embodiments" means that a particular feature, structure or characteristic described in connection with the embodiment may be included in at least one embodiment of the present disclosure. Thus, the appearances of the phrases "in one embodiment" or "in an embodiment" or "in some embodiments" at various places throughout this specification may not necessarily all refer to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

As used herein, the term "resistance" used herein refers to an acquired or natural resistance of cancer cells or a subject to a cancer therapy involving treatment with hypomethylating agent (HMA) including azacitidine (AZA), decitabine (DEC) or a combination thereof i.e., the cancer cells or the subject being non-responsive to or having reduced or limited response, or having a reduced ability of producing a significant response (e.g., partial response and/or complete response) to the therapeutic treatment involving AZA, DEC or a combination thereof. In some embodiments, the resistance may be acquired resistance which arises in the course of a treatment method involving AZA and/or DEC. In some embodiments, the subject has a reduced response to the therapeutic treatment involving administration of AZA and/or DEC, said reduced response being 10% or more, for example, 10%, 20%, 30%, 40%, 50%, 60%, 70%, 80%, 90% or more, to 2-fold, 3-fold, 4-fold, 5-fold, 10-fold, 15-fold, 20-fold or more. The reduction in response to said therapeutic treatment can be measured by comparing with the same cancer sample or subject before the resistance is acquired, or by comparing with a different cancer sample or a subject who is known to have no resistance to said specific therapeutic treatment. A typically acquired resistance to AZA and/or DEC can be mediated by any mechanism. In some embodiments, resistance to AZA and/or DEC is mediated by irregularities or aberrations in glutathione (GSH) signalling pathways. The determination of resistance to the therapeutic treatment involving AZA and/or DEC is routine in the art and within the skill of an ordinarily skilled clinician. For example, resistance can be measured by cell proliferative assays and/or cell death assays.

As used herein, the expression "reversing resistance", "decreasing resistance", "overcoming resistance" or similar expressions as used herein refer to a decrease, reduction, inhibition, prevention or abolition of hypomethylating agent (AZA and/or DEC) resistance in cancer cells in vitro or in vivo, or an enhanced sensitivity to the hypomethylating agent (AZA and/or DEC) in cancer cells in vitro or in vivo. For example, decreasing the resistance to hypomethylating agent may be characterized by a reduction in the amount of AZA or DEC drug used for treating the subject or cancer cells, while achieving the same degree of effectiveness or re-establishing sensitivity to AZA and/or DEC in the subject or cancer cells which had become refractory to said AZA and/or DEC. In some embodiments, decreasing the resistance to hypomethylating agent means increasing the efficacy or sensitivity of AZA or DEC in a subject. In some embodiments, decreasing azacitidine (AZA) resistance means increasing the efficacy or sensitivity of AZA in a subject. In some embodiments, decreasing decitabine (DEC) resistance means increasing the efficacy or sensitivity of DEC in a subject.

As used herein, the expression "combination of: a) sulforaphane, resveratrol and curcumin; and b) hypomethylating agent (HMA) selected from azacitidine (AZA), decitabine (DEC) and a combination thereof" refers to either separate compositions/formulations/dosage forms of a) and b); or both a) and b) provided together as a mixture in a single composition/formulation/dosage form, as long as the effect achieved is commensurate with the intended purpose of the invention, i.e., to synergistically work for treatment of hematological malignancies (MDS or AML) and/or to decrease or overcome resistance to hypomethylating agent (AZA or DEC).

As used herein, the expression "combination of sulforaphane, resveratrol and curcumin" refers to either separate compositions/formulations/dosage forms of each of sulforaphane, resveratrol and curcumin individually, or sulforaphane, resveratrol and curcumin provided together as a mixture in a single composition/formulation/dosage form. Similarly, in some embodiments, when the combination of both azacitidine and decitabine are employed as the hypomethylating agent, either separate compositions/formulations/dosage forms of azacitidine and decitabine are provided, or both azacitidine and decitabine are provided as a mixture in a single composition/formulation/dosage form.

As used herein, the term "genomic aberration", "gene aberration", "gene mutation" or the likes refers to alteration in the nucleotide sequence of the gene such that the altered sequence differs from the sequence of native or naturally occurring gene. In some embodiments, the aberration or mutation can be in any form including but not limited to missense mutation, nonsense mutation, frameshift mutation, insertion mutation, stop-gain mutation, stop-loss mutation, deletion mutation, duplication mutation, repeat expansion, or any combinations thereof.

As used herein, the term "subject" refers to any mammal including, without limitation, a rodent such as mice or rat, a feline, a canine, a human, and other primates (e.g., chimpanzees and other apes and monkey species), farm animals (e.g., cattle, sheep, pigs, goats and horses) and domestic mammals (e.g., dogs and cats). Particularly, the subject according to the invention is a human. In some embodiments, the subject according to the invention has or susceptible to have resistant cancer including MDL or AML.

The term "about" as used herein encompasses variations of +/−10% and more preferably +/−5%, as such variations are appropriate for practicing the present invention.

The present disclosure primarily relates to the field of combination therapy having applications including but not limiting to: 1) decreasing or overcoming resistance to chemotherapeutic agents such as hypomethylating agents in patients suffering from hematological malignancies, thereby augmenting chemotherapy; and 2) ameliorating or treating hematological malignancies and thereby synergistically enhancing the overall treatment in patients. More particularly, the combination therapy comprises employing: a) a therapeutically effective amount of a combination comprising sulforaphane, resveratrol and curcumin; and b) a therapeutically effective amount of hypomethylating agent (HMA) selected from azacitidine (AZA), decitabine (DEC) or a combination thereof. Methods, uses and products employing said combination therapy are provided by the present disclosure.

The disclosure provides a method for decreasing resistance to a hypomethylating agent (HMA) caused by treatment of hematological malignancy in a subject in need thereof, the method comprising administering a therapeutically effective amount of a combination comprising sulforaphane, resveratrol and curcumin to the subject, wherein the hypomethylating agent (HMA) is azacitidine (AZA), or decitabine (DEC), or a combination thereof, and wherein the hematological malignancy is myelodysplastic syndrome (MDS) or acute myeloid leukemia (AML).

In some embodiments, a method is provided for decreasing resistance to azacitidine (AZA) caused by treatment of hematological malignancy in a subject in need thereof, the method comprising administering a therapeutically effective amount of a combination comprising sulforaphane, resveratrol and curcumin to said subject, wherein the hematological malignancy is myelodysplastic syndrome (MDS) or acute myeloid leukemia (AML).

In some embodiments, a method is provided for decreasing resistance to azacitidine (AZA) caused by treatment of acute myeloid leukemia (AML) in a subject in need thereof, the method comprising administering a therapeutically effective amount of a combination comprising sulforaphane, resveratrol and curcumin to said subject.

In some embodiments, a method is provided for decreasing resistance to azacitidine (AZA) caused by treatment of myelodysplastic syndrome (MDS) in a subject in need thereof, the method comprising administering a therapeutically effective amount of a combination comprising sulforaphane, resveratrol and curcumin to said subject.

In some embodiments, a method is provided for decreasing resistance to decitabine (DEC) caused by treatment of hematological malignancy in a subject in need thereof, the method comprising administering a therapeutically effective amount of a combination comprising sulforaphane, resveratrol and curcumin to said subject, wherein the hematological malignancy is myelodysplastic syndrome (MDS) or acute myeloid leukemia (AML).

In some embodiments of the above described method for decreasing resistance, the subject has already been administered with a therapeutically effective amount of the hypomethylating agent (HMA). In some embodiments of the above described method for decreasing resistance, the subject has already been administered with a therapeutically effective amount of azacitidine. In some embodiments of the above described method for decreasing resistance, the subject has already been administered with a therapeutically effective amount of decitabine.

In some embodiments of the above described method for decreasing resistance, the subject is undergoing treatment with a therapeutically effective amount of the hypomethylating agent (HMA). In some embodiments of the above described method for decreasing resistance, the subject is undergoing treatment with a therapeutically effective amount of azacitidine. In some embodiments of the above described method for decreasing resistance, the subject is undergoing treatment with a therapeutically effective amount of decitabine.

In some embodiments of the above described method for decreasing resistance, decreasing resistance comprises improving sensitivity of the subject to the hypomethylating agent (HMA).

In some embodiments of the above described method for decreasing resistance, decreasing resistance comprises improving sensitivity of the subject to azacitidine by administering the combination comprising sulforaphane, resveratrol and curcumin to said subject. In some embodiments of the above described method for decreasing resistance, decreasing resistance comprises improving sensitivity of the subject to decitabine by administering a combination comprising sulforaphane, resveratrol and curcumin to said subject.

In some embodiments of the above described method for decreasing resistance, decreasing resistance comprises improving sensitivity of the subject to azacitidine by administering the combination comprising sulforaphane, resveratrol and curcumin to said subject during treatment of the hematological malignancy when compared to sensitivity of the subject to azacitidine prior to administering the combination.

In some embodiments of the above described method for decreasing resistance, the method comprising administering the combination comprising sulforaphane, resveratrol and curcumin to the subject has an enhanced or synergistic therapeutic effect in the treatment of myelodysplastic syndrome (MDS) or acute myeloid leukemia (AML) when compared to the effect of administering azacitidine alone.

In some embodiments of the above described method for decreasing resistance, the method comprising administering the combination comprising sulforaphane, resveratrol and curcumin to the subject has an enhanced or synergistic therapeutic effect in the treatment of myelodysplastic syndrome (MDS) or acute myeloid leukemia (AML) when compared to the effect of administering decitabine alone.

In some embodiments of the above described method for decreasing resistance, the combination comprising sulforaphane, resveratrol and curcumin is administered as a single formulation consisting of sulforaphane, resveratrol, curcumin and a pharmaceutically acceptable excipient.

In some embodiments of the above described method for decreasing resistance, the combination comprising sulforaphane, resveratrol and curcumin is administered as separate formulations of:
I. sulforaphane and a pharmaceutically acceptable excipient,
II. resveratrol and a pharmaceutically acceptable excipient, and
III. curcumin and a pharmaceutically acceptable excipient.

In some embodiments of the above described method for decreasing resistance, the hypomethylating agent (HMA) is administered as a formulation comprising the hypomethylating agent (HMA) and a pharmaceutically acceptable excipient.

In some embodiments of the above described method for decreasing resistance, the azacitidine is administered as a formulation comprising azacitidine and a pharmaceutically acceptable excipient.

In some embodiments of the above described method for decreasing resistance, the decitabine is administered as a formulation comprising decitabine and a pharmaceutically acceptable excipient.

In some embodiments of the above described method for decreasing resistance, the hypomethylating agent (HMA) is administered as a formulation comprising azacitidine, decitabine and a pharmaceutically acceptable excipient.

In some embodiments of the above described method for decreasing resistance, the pharmaceutically acceptable excipient is selected from the group comprising carrier, binder, encapsulant, coating, color, preservative, lubricant, disintegrant, saline, gelling agent and combinations thereof.

In some embodiments of the above described method for decreasing resistance, the carrier is selected from the group comprising but not limited to Micelles, Liposomes, Polymeric particles, Hydrogels, Inorganic/solid particles, Dendrimers, Nanospheres/nanocapsules, Quantum dots and combinations thereof.

In some embodiments of the above described method for decreasing resistance, the binder or encapsulant is selected from the group comprising but not limited to Sucrose, Liquid glucose, Acacia, Tragacanth, Gelatin, Starch Paste, Pregelatinized starch, Alginic acid, Cellulose, Methyl cellulose, Ethyl cellulose, Hydroxypropylmethyl cellulose, Hydroxypropyl cellulose, Sodium carboxymethyl cellulose, Polyvinyl pyrrolidone, Polyethylene glycol, Polyvinyl alcohol, Polymethacrylate and combinations thereof.

In some embodiments of the above described method for decreasing resistance, the coating is selected from the group comprising but not limited to Fatty acids, Wax, Shellac, Polymer, Plant fibers and combinations thereof.

In some embodiments of the above described method for decreasing resistance, the color is selected from the group comprising but not limited to Azo dye, Xanthene dye, Pyralozone dye, Indigoid dye, Triarylmethane dye, Carotenoid, Chlorophyllin, Anthocyanin, Betanin and combinations thereof.

In some embodiments of the above described method for decreasing resistance, the preservative is selected from the group comprising but not limited to Sorbic acid and its salts or derivatives, Benzoic acid and its salts or derivatives, Parabens, Sulfur dioxide or sulfites, Nitrites, Nitrates, Lactic acid, Propionic acid or propionates, Isothiazolinones, Ascorbic acid and its salts or derivatives, Butylated hydroxytoluene, Butylated hydroxyanisole, Gallic acid and its salts or derivatives, Tocopherols, Thimerosal, Phenol, 2-Phenoxyethanol, Benzethonium chloride, Disodium ethylenediaminetetraacetic acid, Polyphosphates, Citric acid and its salts or derivatives, Sodium chloride, Methyl paraben and combinations thereof.

In some embodiments of the above described method for decreasing resistance, the lubricant is selected from the group comprising but not limited to Boric acid and its esters or salts, Oleic acid and its esters or salts, Stearic acid and its esters or salts, Palmitic acid and its esters or salts, Myristic acid and its esters or salts, Hydrated magnesium silicate (talc), Polyethylene glycol, Sodium acetate, Wax, Glyceryl behenate and combinations thereof.

In some embodiments of the above described method for decreasing resistance, the disintegrant is selected from the group comprising but not limited to Starch, Pregelatinized starch, Sodium croscarmellose, Crospovidone, Sodium starch glycolate and combinations thereof.

In some embodiments of the above described method for decreasing resistance, the gelling agent is selected from the group comprising but not limited to Tragacanth, Pectin, Starch, Carbomer, Sodium alginate, Gelatin, Cellulose or its derivatives, Polyvinylalcohol, Agar, Chitosan, Xanthan and combinations thereof.

In some embodiments of the above described method for decreasing resistance, the resistance to hypomethylating agent (HMA) is caused by genomic aberration in at least one gene selected from tet methylcytosine dioxygenase 2 (TET2), ASXL transcriptional regulator 1 (ASXL1), and a combination thereof.

In some embodiments of the above described method for decreasing resistance, the aberration in tet methylcytosine dioxygenase 2 (TET2) comprises any aberration which leads to loss of function of TET2 gene. In some embodiments, said aberration is selected from the group comprising missense mutation, nonsense mutation, frameshift mutation, insertion mutation, stop-gain mutation, stop-loss mutation, deletion mutation, duplication mutation, repeat expansion and any combinations thereof.

In some embodiments of the above described method for decreasing resistance, the aberration in ASXL transcriptional regulator 1 (ASXL1) comprises any aberration which leads to loss of function of ASXL1 gene. In some embodiments, said aberration is selected from the group comprising missense mutation, nonsense mutation, frameshift mutation, insertion mutation, stop-gain mutation, stop-loss mutation, deletion mutation, duplication mutation, repeat expansion and any combinations thereof.

In some embodiments of the above described method for decreasing resistance, the resistance to hypomethylating agent (HMA) is caused by genomic aberration in tet methylcytosine dioxygenase 2 (TET2).

In some embodiments of the above described method for decreasing resistance, the resistance to hypomethylating agent (HMA) is caused by genomic aberration in ASXL transcriptional regulator 1 (ASXL1).

In some embodiments of the above described method for decreasing resistance, the resistance to hypomethylating agent (HMA) is caused by genomic aberration in tet methylcytosine dioxygenase 2 (TET2) and ASXL transcriptional regulator 1 (ASXL1).

In some embodiments of the above described method for decreasing resistance, the sulforaphane, the resveratrol and the curcumin are derived from plants. In some embodiments, the sulforaphane, the resveratrol and the curcumin are plant extracts. In some embodiments, the sulforaphane, the resveratrol and the curcumin are individually obtained as plant extracts and are employed for administration as a combination either in purified or unpurified forms.

In some embodiments of the above described method for decreasing resistance, the combination comprising sulforaphane, resveratrol and curcumin is administered at a therapeutically effective amount ranging from 0.05 mg/kg body weight to 10 mg/kg body weight, including all values and ranges therebetween. In some embodiments of the above described method for decreasing resistance, the combination comprising sulforaphane, resveratrol and curcumin is administered at a therapeutically effective amount of about 0.05 mg to 0.3 mg/kg body weight of sulforaphane, about 2.5 mg to 10 mg/kg body weight of resveratrol, and about 2.5 mg to 10 mg/kg body weight of curcumin, including all values and ranges therebetween. In some embodiments of the above described method for decreasing resistance, the combination comprising sulforaphane, resveratrol and curcumin is administered at a therapeutically effective amount of about 5 mg-30 mg of sulforaphane, about 250 mg-1000 mg of resveratrol, and about 250 mg-1000 mg of curcumin, including all values and ranges therebetween. In some embodiments, said combination comprising sulforaphane, resveratrol and curcumin is administered daily to the subject.

In some embodiments of the above described method for decreasing resistance, the sulforaphane in the combination comprising sulforaphane, resveratrol and curcumin is administered at a therapeutically effective amount ranging from about 0.05 mg/kg body weight to 0.3 mg/kg body weight, including all values and ranges therebetween. In some embodiments of the above described method for decreasing resistance, the sulforaphane in the combination comprising sulforaphane, resveratrol and curcumin is administered at a therapeutically effective amount of about 5 mg-30 mg, including all values and ranges therebetween. In some embodiments, said sulforaphane is administered daily to the subject.

In some embodiments of the above described method for decreasing resistance, the resveratrol in the combination comprising sulforaphane, resveratrol and curcumin is administered at a therapeutically effective amount ranging from about 2.5 mg/kg body weight to 10 mg/kg body weight, including all values and ranges therebetween. In some embodiments of the above described method for decreasing resistance, the resveratrol in the combination comprising sulforaphane, resveratrol and curcumin is administered at a therapeutically effective amount of about 250 mg-1000 mg, including all values and ranges therebetween. In some embodiments, said resveratrol is administered daily to the subject.

In some embodiments of the above described method for decreasing resistance, the curcumin in the combination comprising sulforaphane, resveratrol and curcumin is administered at a therapeutically effective amount ranging from about 2.5 mg/kg body weight to 10 mg/kg body weight, including all values and ranges therebetween. In some embodiments of the above described method for decreasing resistance, the curcumin in the combination comprising sulforaphane, resveratrol and curcumin is administered at a therapeutically effective amount of about 250 mg-1000 mg of curcumin, including all values and ranges therebetween. In some embodiments, said curcumin is administered daily to the subject.

In some embodiments of the above described method for decreasing resistance, the combination comprising sulforaphane, resveratrol and curcumin is administered as 1 dose per day in a single peroral formulation which comprises sulforaphane at 5-30 mg, resveratrol at 250-1000 mg and curcumin at 250-1000 mg. In some embodiments of the above described method for decreasing resistance, the combination comprising sulforaphane, resveratrol and curcumin is administered as 1 dose per day as separate peroral formulations of: a) a formulation comprising sulforaphane at 5-30 mg, b) a formulation comprising resveratrol at 250-1000 mg, and c) a formulation comprising curcumin at 250-1000 mg.

In some embodiments of the above described method for decreasing resistance, the combination comprising sulforaphane, resveratrol and curcumin is administered as 1 dose per day in a single intravenous (i.v.) formulation which comprises sulforaphane at 5-30 mg, resveratrol at 250-1000 mg and curcumin at 250-1000 mg. In some embodiments of the above described method for decreasing resistance, the combination comprising sulforaphane, resveratrol and curcumin is administered as 1 dose per day as separate intravenous (i.v.) formulations of: a) a formulation comprising sulforaphane at 5-30 mg, b) a formulation comprising resveratrol at 250-1000 mg, and c) a formulation comprising curcumin at 250-1000 mg.

In some embodiments of the above described method for decreasing resistance, the combination comprising sulforaphane, resveratrol and curcumin is administered as 1 dose per day in a single subcutaneous (s.c.) formulation which comprises sulforaphane at 5-30 mg, resveratrol at 250-1000 mg and curcumin at 250-1000 mg. In some embodiments of the above described method for decreasing resistance, the combination comprising sulforaphane, resveratrol and curcumin is administered as 1 dose per day as separate subcutaneous (s.c.) formulations of: a) a formulation comprising sulforaphane at 5-30 mg, b) a formulation comprising resveratrol at 250-1000 mg, and c) a formulation comprising curcumin at 250-1000 mg.

In some embodiments of the above described method for decreasing resistance, the hypomethylating agent (HMA) is administered at a therapeutically effective amount ranging from about 0.2 mg/kg body weight to 12 mg/kg body weight, including all values and ranges therebetween. In some embodiments of the above described method for decreasing resistance, the hypomethylating agent (HMA) is administered at an amount ranging from about 0.2 mg/kg body weight to 12 mg/kg body weight in a therapeutic regimen having 28 days as each cycle and consisting of administration of 5+2+2 (seven subcutaneous injections), and said regimen comprising at least 4 cycles. In some embodiments of the above described method for decreasing resistance, the hypomethylating agent (HMA) is administered at an amount of about 1.5 mg/kg body weight in a therapeutic regimen having 28 days as each cycle and consisting of administration of 5+2+2 (seven subcutaneous injections), and said regimen comprising at least 4 cycles.

In some embodiments of the above described method for decreasing resistance, the azacitidine is administered at a therapeutically effective amount ranging from 1.5 mg/kg body weight to 12 mg/kg body weight, including all values and ranges therebetween. In some embodiments of the above described method for decreasing resistance, the azacitidine is administered at an amount ranging from about 1.5 mg/kg body weight to 12 mg/kg body weight in a therapeutic regimen having 28 days as each cycle and consisting of administration of 5+2+2 (seven subcutaneous injections), and said regimen comprising at least 4 cycles. In some embodiments of the above described method for decreasing resistance, the azacitidine is administered at an amount of about 1.5 mg/kg body weight in a therapeutic regimen having 28 days as each cycle and consisting of administration of 5+2+2 (seven subcutaneous injections), and said regimen comprising at least 4 cycles.

In some embodiments of the above described method for decreasing resistance, the decitabine is administered at a therapeutically effective amount ranging from 0.2 mg/kg body weight to 2.5 mg/kg body weight, including all values and ranges therebetween. In some embodiments of the above described method for decreasing resistance, the decitabine is administered at an amount ranging from about 0.2 mg/kg body weight to 2.5 mg/kg body weight in a therapeutic regimen having 28 days as each cycle and consisting of administration of 5+2+2 (seven subcutaneous injections), and said regimen comprising at least 4 cycles. In some embodiments of the above described method for decreasing resistance, the decitabine is administered at an amount of about 1.5 mg/kg body weight in a therapeutic regimen having 28 days as each cycle and consisting of administration of 5+2+2 (seven subcutaneous injections), and said regimen comprising at least 4 cycles.

In some embodiments of the above described method for decreasing resistance, the method comprises administering the combination comprising sulforaphane, resveratrol and curcumin, to the subject orally or parenterally, or a combination of both oral and parenteral administration. In some embodiments of the above described method for decreasing resistance, the method comprises administering the hypomethylating agent(s) to the subject orally, parenterally or topically, or any combination thereof, for example, a combination of oral and parenteral administration or a combination of topical and parenteral administration.

In embodiments where the formulation of the combination comprising sulforaphane, resveratrol and curcumin (a single formulation or separate formulations of sulforaphane, resveratrol and curcumin) and the formulation of the hypomethylating agent (eg. azacitidine) are administered as separate formulations, all formulations can be administered using the same route of administration (e.g., orally or parenterally) or one formulation can be administered using one route of administration (e.g., orally or parenterally) and the other formulation(s) can be administered using the other routes of administration (e.g., if one is administered orally, the other is administered parenterally or vice versa).

In some embodiments, parenteral administration comprises administration via injection or infusion. In some embodiments, parenteral administration is selected from intraperitoneal, intravenous, intramuscular, intradermal, subcutaneous, intraosseal, intratumoral, intralesional and intrathecal administration. In some embodiments, parenteral administration is administration via intraperitoneal injection. In some embodiments, parenteral administration is administration via intravenous infusion.

In some embodiments, oral administration comprises administration via tablets, capsules, drops, mouth wash, mouth spray or any combinations thereof.

In some embodiments, topical administration comprises administration via creams, ointments, gels, gauze or in liquid form such as oils or tinctures, rectal or vaginal use such as suppositories, or any combinations thereof.

In some embodiments, the combination comprising sulforaphane, resveratrol and curcumin is formulated for oral administration. In some embodiments, the hypomethylating agent (HMA) is formulated for parenteral administration. In some embodiments, the azacitidine is formulated for intraperitoneal administration.

The single formulation or separate formulations as described herein can be any pharmaceutically acceptable dosage forms. In some embodiments, pharmaceutically acceptable dosage forms are selected from an oral dosage form or a parenteral dosage form. Oral dosage forms can be discrete units, such as hard or soft capsules, tablets, pills, or lozenges; or a liquid form such as emulsions, solutions, suspensions, syrups, and elixirs. Parenteral dosage forms can be a liquid form such as emulsions, solutions, and suspensions or a solid form packaged in a single-dose or multidose containers that is reconstituted prior to administration. In some embodiments, parenteral dosage form is a ready-to-use (RTU) liquid form.

In some embodiments of the above described method for decreasing resistance, the subject is a mammal. In some embodiments of the above described method for decreasing resistance, the subject is a human.

In some embodiments of the above described method for decreasing resistance, the subject is a human patient who has developed resistance to treatment with hypomethylating agent (HMA). In some embodiments of the above described method for decreasing resistance, the subject is a human patient who has developed resistance to treatment with azacitidine.

In some embodiments of the above described method for decreasing resistance, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof.

In some embodiments of the above described method for decreasing resistance, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce side effects of the hypomethylating agent (HMA).

In some embodiments of the above described method for decreasing resistance, said method further comprises orally administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce side effects of the hypomethylating agent (HMA).

In some embodiments of the above described method for decreasing resistance to hypomethylating agent (HMA) in a subject with myelodysplastic syndrome (MDS) or acute myeloid leukemia (AML) undergoing HMA treatment, said method further comprises administering a combination comprising:
　a) a therapeutically effective amount of sulforaphane, resveratrol and curcumin; and
　b) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
　wherein b) is administered orally to reduce side effects of the hypomethylating agent (HMA).

In some embodiments of the above described method for decreasing resistance to hypomethylating agent (HMA) in a subject with myelodysplastic syndrome (MDS) or acute myeloid leukemia (AML) undergoing HMA treatment, said method further comprises administering a combination comprising:
　a) a therapeutically effective amount of sulforaphane, resveratrol and curcumin; and
　b) a therapeutically effective amount of cannabidiol (CBD), cannabigerol (CBG), cannabinol (CBN), cannabidivarin (CBDV), cannabichromene (CBC) and tetrahydrocannabivarin (THCV),
　wherein b) is administered orally to reduce side effects of the hypomethylating agent (HMA).

In some embodiments of the above described method for decreasing resistance, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce the inflammatory response of the tissue to the hypomethylating agent (HMA).

In some embodiments of the above described method for decreasing resistance, said method further comprises topically administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce the inflammatory response of the tissue to the hypomethylating agent (HMA).

In some embodiments of the above described method for decreasing resistance, said method further comprises topically administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to the area of subcutaneous application of the HMA to reduce the inflammatory response of the tissue to the HMA.

In some embodiments of the above described method for decreasing resistance to hypomethylating agent (HMA) in a subject with myelodysplastic syndrome (MDS) or acute myeloid leukemia (AML) undergoing HMA treatment, said method further comprises administering a combination comprising:
　a) a therapeutically effective amount of sulforaphane, resveratrol and curcumin; and
　b) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
　wherein b) is administered topically to the area of subcutaneous application of the hypomethylating agent (HMA) to reduce the inflammatory response of the tissue to the hypomethylating agent (HMA).

In some embodiments of the above described method for decreasing resistance to hypomethylating agent (HMA) in a subject with myelodysplastic syndrome (MDS) or acute myeloid leukemia (AML) undergoing HMA treatment, said method further comprises administering a combination comprising:
- a) a therapeutically effective amount of sulforaphane, resveratrol and curcumin; and
- b) a therapeutically effective amount of cannabidiol (CBD), cannabigerol (CBG), cannabinol (CBN), cannabidivarin (CBDV), cannabichromene (CBC) and tetrahydrocannabivarin (THCV),
- wherein b) is administered topically to the area of subcutaneous application of the hypomethylating agent (HMA) to reduce the inflammatory response of the tissue to the hypomethylating agent (HMA).

In some embodiments of the above described method for decreasing resistance, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce side effects of the HMA or to reduce the inflammatory response of the tissue to the HMA.

In some embodiments of the above described method for decreasing resistance to hypomethylating agent (HMA) in a subject with myelodysplastic syndrome (MDS) or acute myeloid leukemia (AML) undergoing HMA treatment, said method further comprises administering a combination comprising:
- a) a therapeutically effective amount of sulforaphane, resveratrol and curcumin; and
- b) a therapeutically effective amount of cannabidiol (CBD), cannabigerol (CBG), cannabinol (CBN), cannabidivarin (CBDV), cannabichromene (CBC) and tetrahydrocannabivarin (THCV),
- wherein b) is:
  - i) administered orally to reduce side effects of the HMA, or
  - ii) administered topically to the area of subcutaneous application of the HMA to reduce the inflammatory response of the tissue to the HMA, or
  - iii) administered both orally and topically according to i) and ii).

The present disclosure further provides a method of treating a hematological malignancy selected from myelodysplastic syndrome (MDS) and acute myeloid leukemia (AML) in a subject in need thereof, the method comprising administering:
- a) a therapeutically effective amount of a combination comprising sulforaphane, resveratrol and curcumin; and
- b) a therapeutically effective amount of hypomethylating agent (HMA) selected from azacitidine (AZA), decitabine (DEC) and a combination thereof, to the subject.

In some embodiments of the above described method of treating hematological malignancy, the method comprises treating acute myeloid leukemia (AML) in a subject in need thereof by administering:
- a) a therapeutically effective amount of a combination comprising sulforaphane, resveratrol and curcumin; and
- b) a therapeutically effective amount of azacitidine (AZA), to the subject.

In some embodiments of the above described method of treating hematological malignancy, the method comprises treating myelodysplastic syndrome (MDS) in a subject in need thereof by administering:
- a) a therapeutically effective amount of a combination comprising sulforaphane, resveratrol and curcumin; and
- b) a therapeutically effective amount of azacitidine (AZA), to the subject.

In some embodiments of the above described method of treating hematological malignancy, the method comprises treating myelodysplastic syndrome (MDS) or acute myeloid leukemia (AML) in a subject in need thereof by administering:
- a) a therapeutically effective amount of a combination comprising sulforaphane, resveratrol and curcumin; and
- b) a therapeutically effective amount of decitabine (DEC), to the subject.

In some embodiments of the above described method of treating hematological malignancy, wherein: a) a therapeutically effective amount of a combination comprising sulforaphane, resveratrol and curcumin, and b) a therapeutically effective amount of azacitidine (AZA) or decitabine (DEC) or a combination thereof, are administered concurrently, sequentially, or at different time intervals. In some embodiments, both a) and b) are administered concurrently.

In some embodiments, both a) and b) are administered sequentially i.e. one after the other. In some embodiments, both a) and b) are administered concurrently. In some embodiments, both a) and b) are administered at different time intervals.

In some embodiments of the above described method of treating hematological malignancy, the subject has already been administered with a therapeutically effective amount of the hypomethylating agent (HMA). In some embodiments of the above described method of treating hematological malignancy, the subject has already been administered with a therapeutically effective amount of azacitidine. In some embodiments of the above described method of treating hematological malignancy, the subject has already been administered with a therapeutically effective amount of decitabine.

In some embodiments of the above described method of treating hematological malignancy, the subject is undergoing treatment with a therapeutically effective amount of the hypomethylating agent (HMA). In some embodiments of the above described method of treating hematological malignancy, the subject is undergoing treatment with a therapeutically effective amount of azacitidine. In some embodiments of the above described method of treating hematological malignancy, the subject is undergoing treatment with a therapeutically effective amount of decitabine.

In some embodiments of the above described method of treating hematological malignancy, the method comprising administering a) and b) has an enhanced or synergistic therapeutic effect in the treatment of hematological malignancy compared to the effect of hypomethylating agent (HMA) when administered alone.

In some embodiments of the above described method of treating hematological malignancy, the method comprising administering a) and b) has a synergistic therapeutic effect in the treatment of hematological malignancy compared to the effect of administering azacitidine alone.

In some embodiments of the above described method of treating hematological malignancy, the method comprising administering a) and b) has a synergistic therapeutic effect in the treatment of hematological malignancy compared to the effect of administering azacitidine and any one compound selected from sulforaphane, resveratrol and curcumin.

In some embodiments of the above described method of treating hematological malignancy, the method comprising administering a) and b) has a synergistic therapeutic effect in the treatment of hematological malignancy compared to the effect of administering azacitidine and any two compounds selected from sulforaphane, resveratrol and curcumin.

In some embodiments of the above described method of treating hematological malignancy, the method improves sensitivity of the subject to the hypomethylating agent (HMA) during treatment of the hematological malignancy. In some embodiments, the method improves sensitivity of the subject to azacitidine during treatment of the hematological malignancy. In some embodiments, the method improves sensitivity of the subject to azacitidine during treatment of AML. In some embodiments, the method improves sensitivity of the subject to azacitidine during treatment of MDS. In some embodiments, the method improves sensitivity of the subject to decitabine during treatment of the hematological malignancy selected from MDS and AML.

In some embodiments of the above described method of treating hematological malignancy, the combination comprising sulforaphane, resveratrol and curcumin is administered as a single formulation consisting of sulforaphane, resveratrol, curcumin and a pharmaceutically acceptable excipient.

In some embodiments of the above described method of treating hematological malignancy, the combination comprising sulforaphane, resveratrol and curcumin is administered as separate formulations of:
I. sulforaphane and a pharmaceutically acceptable excipient,
II. resveratrol and a pharmaceutically acceptable excipient, and
III. curcumin and a pharmaceutically acceptable excipient.

In some embodiments of the above described method of treating hematological malignancy, the hypomethylating agent (HMA) is administered as a formulation comprising the hypomethylating agent (HMA) and a pharmaceutically acceptable excipient.

In some embodiments of the above described method of treating hematological malignancy, the azacitidine is administered as a formulation comprising azacitidine and a pharmaceutically acceptable excipient.

In some embodiments of the above described method of treating hematological malignancy, the decitabine is administered as a formulation comprising decitabine and a pharmaceutically acceptable excipient.

In some embodiments of the above described method of treating hematological malignancy, the pharmaceutically acceptable excipient is selected from the group comprising carrier, binder, encapsulant, coating, color, preservative, lubricant, disintegrant, saline, gelling agent and combinations thereof.

In some embodiments of the above described method of treating hematological malignancy, the carrier is selected from the group comprising but not limited to Micelles, Liposomes, Polymeric particles, Hydrogels, Inorganic/solid particles, Dendrimers, Nanospheres/nanocapsules, Quantum dots and combinations thereof.

In some embodiments of the above described method of treating hematological malignancy, the binder or encapsulant is selected from the group comprising but not limited to Sucrose, Liquid glucose, Acacia, Tragacanth, Gelatin, Starch Paste, Pregelatinized starch, Alginic acid, Cellulose, Methyl cellulose, Ethyl cellulose, Hydroxypropylmethyl cellulose, Hydroxypropyl cellulose, Sodium carboxymethyl cellulose, Polyvinyl pyrrolidone, Polyethylene glycol, Polyvinyl alcohol, Polymethacrylate and combinations thereof.

In some embodiments of the above described method of treating hematological malignancy, the coating is selected from the group comprising but not limited to Fatty acids, Wax, Shellac, Polymer, Plant fibers and combinations thereof.

In some embodiments of the above described method of treating hematological malignancy, the color is selected from the group comprising but not limited to Azo dye, Xanthene dye, Pyralozone dye, Indigoid dye, Triarylmethane dye, Carotenoid, Chlorophyllin, Anthocyanin, Betanin and combinations thereof.

In some embodiments of the above described method of treating hematological malignancy, the preservative is selected from the group comprising but not limited to Sorbic acid and its salts or derivatives, Benzoic acid and its salts or derivatives, Parabens, Sulfur dioxide or sulfites, Nitrites, Nitrates, Lactic acid, Propionic acid or propionates, Isothiazolinones, Ascorbic acid and its salts or derivatives, Butylated hydroxytoluene, Butylated hydroxyanisole, Gallic acid and its salts or derivatives, Tocopherols, Thimerosal, Phenol, 2-Phenoxyethanol, Benzethonium chloride, Disodium ethylenediaminetetraacetic acid, Polyphosphates, Citric acid and its salts or derivatives, Sodium chloride, Methyl paraben and combinations thereof.

In some embodiments of the above described method of treating hematological malignancy, the lubricant is selected from the group comprising but not limited to Boric acid and its esters or salts, Oleic acid and its esters or salts, Stearic acid and its esters or salts, Palmitic acid and its esters or salts, Myristic acid and its esters or salts, Hydrated magnesium silicate (talc), Polyethylene glycol, Sodium acetate, Wax, Glyceryl behenate and combinations thereof.

In some embodiments of the above described method of treating hematological malignancy, the disintegrant is selected from the group comprising but not limited to Starch, Pregelatinized starch, Sodium croscarmellose, Crospovidone, Sodium starch glycolate and combinations thereof.

In some embodiments of the above described method of treating hematological malignancy, the gelling agent is selected from the group comprising but not limited to Tragacanth, Pectin, Starch, Carbomer, Sodium alginate, Gelatin, Cellulose or its derivatives, Polyvinylalcohol, Agar, Chitosan, Xanthan and combinations thereof.

In some embodiments of the above described method of treating hematological malignancy, the resistance to hypomethylating agent (HMA) is caused by genomic aberration in at least one gene selected from tet methylcytosine dioxygenase 2 (TET2), ASXL transcriptional regulator 1 (ASXL1), and a combination thereof.

In some embodiments of the above described method of treating hematological malignancy, the aberration in tet methylcytosine dioxygenase 2 (TET2) comprises any aberration which leads to loss of function of TET2 gene. In some embodiments, said aberration is selected from the group comprising missense mutation, nonsense mutation, frameshift mutation, insertion mutation, stop-gain mutation, stop-loss mutation, deletion mutation, duplication mutation, repeat expansion and any combinations thereof.

In some embodiments of the above described method of treating hematological malignancy, the aberration in ASXL transcriptional regulator 1 (ASXL1) comprises any aberration which leads to loss of function of ASXL1gene. In some embodiments, said aberration is selected from the group comprising missense mutation, nonsense mutation, frameshift mutation, insertion mutation, stop-gain mutation, stop-loss mutation, deletion mutation, duplication mutation, repeat expansion and any combinations thereof.

In some embodiments of the above described method of treating hematological malignancy, the resistance to hypomethylating agent (HMA) is caused by genomic aberration in tet methylcytosine dioxygenase 2 (TET2).

In some embodiments of the above described method of treating hematological malignancy, the resistance to hypomethylating agent (HMA) is caused by genomic aberration in ASXL transcriptional regulator 1 (ASXL1).

In some embodiments of the above described method of treating hematological malignancy, the resistance to hypomethylating agent (HMA) is caused by genomic aberration in tet methylcytosine dioxygenase 2 (TET2) and ASXL transcriptional regulator 1 (ASXL1).

In some embodiments of the above described method of treating hematological malignancy, the sulforaphane, the resveratrol and the curcumin are derived from plants. In some embodiments, the sulforaphane, the resveratrol and the curcumin are plant extracts. In some embodiments, the sulforaphane, the resveratrol and the curcumin are individually obtained as plant extracts and are employed for administration as a combination either in purified or unpurified forms.

In some embodiments of the above described method of treating hematological malignancy, the combination comprising sulforaphane, resveratrol and curcumin is administered at a therapeutically effective amount ranging from 0.05 mg/kg body weight to 10 mg/kg body weight, including all values and ranges therebetween. In some embodiments of the above described method of treating hematological malignancy, the combination comprising sulforaphane, resveratrol and curcumin is administered at a therapeutically effective amount of about 0.05 mg to 0.3 mg/kg body weight of sulforaphane, about 2.5 mg to 10 mg/kg body weight of resveratrol, and about 2.5 mg to 10 mg/kg body weight of curcumin, including all values and ranges therebetween. In some embodiments of the above described method of treating hematological malignancy, the combination comprising sulforaphane, resveratrol and curcumin is administered at a therapeutically effective amount of about 5 mg-30 mg of sulforaphane, about 250 mg-1000 mg of resveratrol, and about 250 mg-1000 mg of curcumin, including all values and ranges therebetween. In some embodiments, said combination comprising sulforaphane, resveratrol and curcumin is administered daily to the subject.

In some embodiments of the above described method of treating hematological malignancy, the sulforaphane in the combination comprising sulforaphane, resveratrol and curcumin is administered at a therapeutically effective amount ranging from about 0.05 mg/kg body weight to 0.3 mg/kg body weight, including all values and ranges therebetween. In some embodiments of the above described method of treating hematological malignancy, the sulforaphane in the combination comprising sulforaphane, resveratrol and curcumin is administered at a therapeutically effective amount of about 5 mg-30 mg, including all values and ranges therebetween. In some embodiments, said sulforaphane is administered daily to the subject.

In some embodiments of the above described method of treating hematological malignancy, the resveratrol in the combination comprising sulforaphane, resveratrol and curcumin is administered at a therapeutically effective amount ranging from about 2.5 mg/kg body weight to 10 mg/kg body weight, including all values and ranges therebetween.

In some embodiments of the above described method of treating hematological malignancy, the resveratrol in the combination comprising sulforaphane, resveratrol and curcumin is administered at a therapeutically effective amount of about 250 mg-1000 mg, including all values and ranges therebetween. In some embodiments, said resveratrol is administered daily to the subject.

In some embodiments of the above described method of treating hematological malignancy, the curcumin in the combination comprising sulforaphane, resveratrol and curcumin is administered at a therapeutically effective amount ranging from about 2.5 mg/kg body weight to 10 mg/kg body weight, including all values and ranges therebetween. In some embodiments of the above described method of treating hematological malignancy, the curcumin in the combination comprising sulforaphane, resveratrol and curcumin is administered at a therapeutically effective amount of about 250 mg-1000 mg of curcumin, including all values and ranges therebetween. In some embodiments, said curcumin is administered daily to the subject.

In some embodiments of the above described method of treating hematological malignancy, the combination comprising sulforaphane, resveratrol and curcumin is administered as 1 dose per day in a single peroral formulation which comprises sulforaphane at 5-30 mg, resveratrol at 250-1000 mg and curcumin at 250-1000 mg. In some embodiments of the above described method of treating hematological malignancy, the combination comprising sulforaphane, resveratrol and curcumin is administered as 1 dose per day as separate peroral formulations of: a) a formulation comprising sulforaphane at 5-30 mg, b) a formulation comprising resveratrol at 250-1000 mg, and c) a formulation comprising curcumin at 250-1000 mg.

In some embodiments of the above described method of treating hematological malignancy, the combination comprising sulforaphane, resveratrol and curcumin is administered as 1 dose per day in a single intravenous (i.v.) formulation which comprises sulforaphane at 5-30 mg, resveratrol at 250-1000 mg and curcumin at 250-1000 mg. In some embodiments of the above described method of treating hematological malignancy, the combination comprising sulforaphane, resveratrol and curcumin is administered as 1 dose per day as separate intravenous (i.v.) formulations of: a) a formulation comprising sulforaphane at 5-30 mg, b) a formulation comprising resveratrol at 250-1000 mg, and c) a formulation comprising curcumin at 250-1000 mg.

In some embodiments of the above described method of treating hematological malignancy, the combination comprising sulforaphane, resveratrol and curcumin is administered as 1 dose per day in a single subcutaneous (s.c.) formulation which comprises sulforaphane at 5-30 mg, resveratrol at 250-1000 mg and curcumin at 250-1000 mg. In some embodiments of the above described method of treating hematological malignancy, the combination comprising sulforaphane, resveratrol and curcumin is administered as 1 dose per day as separate subcutaneous (s.c.) formulations of: a) a formulation comprising sulforaphane at 5-30 mg, b) a formulation comprising resveratrol at 250-1000 mg, and c) a formulation comprising curcumin at 250-1000 mg.

In some embodiments of the above described method of treating hematological malignancy, the hypomethylating agent (HMA) is administered at a therapeutically effective amount ranging from about 0.2 mg/kg body weight to 12 mg/kg body weight, including all values and ranges therebetween. In some embodiments of the above described method of treating hematological malignancy, the hypomethylating agent (HMA) is administered at an amount ranging from about 0.2 mg/kg body weight to 12 mg/kg body weight in a therapeutic regimen having 28 days as each cycle and consisting of administration of 5+2+2 (seven subcutaneous injections), and said regimen comprising at least 4 cycles. In some embodiments of the above described method of treating hematological malignancy, the hypomethylating agent (HMA) is administered at an amount of about 1.5 mg/kg body weight in a therapeutic regimen having 28 days as each cycle and consisting of administration of 5+2+2 (seven subcutaneous injections), and said regimen comprising at least 4 cycles.

In some embodiments of the above described method of treating hematological malignancy, the azacitidine is administered at a therapeutically effective amount ranging from 1.5 mg/kg body weight to 12 mg/kg body weight, including all values and ranges therebetween. In some embodiments of the above described method of treating hematological malignancy, the azacitidine is administered at an amount ranging from about 1.5 mg/kg body weight to 12 mg/kg body weight in a therapeutic regimen having 28 days as each cycle and consisting of administration of 5+2+2 (seven subcutaneous injections), and said regimen comprising at least 4 cycles. In some embodiments of the above described method of treating hematological malignancy, the azacitidine is administered at an amount of about 1.5 mg/kg body weight in a therapeutic regimen having 28 days as each cycle and consisting of administration of 5+2+2 (seven subcutaneous injections), and said regimen comprising at least 4 cycles.

In some embodiments of the above described method of treating hematological malignancy, the decitabine is administered at a therapeutically effective amount ranging from 0.2 mg/kg body weight to 2.5 mg/kg body weight, including all values and ranges therebetween. In some embodiments of the above described method of treating hematological malignancy, the decitabine is administered at an amount ranging from about 0.2 mg/kg body weight to 2.5 mg/kg body weight in a therapeutic regimen having 28 days as each cycle and consisting of administration of 5+2+2 (seven subcutaneous injections), and said regimen comprising at least 4 cycles. In some embodiments of the above described method of treating hematological malignancy, the decitabine is administered at an amount of about 0.2 mg/kg body weight in a therapeutic regimen having 28 days as each cycle and consisting of administration of 5+2+2 (seven subcutaneous injections), and said regimen comprising at least 4 cycles.

In some embodiments of the above described method of treating hematological malignancy:
a) the combination of sulforaphane, resveratrol and curcumin is administered at a therapeutically effective amount ranging from 0.05 mg/kg body weight to 10 mg/kg body weight, including all values and ranges therebetween; and
b) the hypomethylating agent (HMA) is administered at a therapeutically effective amount ranging from about 0.2 mg/kg body weight to 12 mg/kg body weight, including all values and ranges therebetween.

In some embodiments of the above described method of treating hematological malignancy:
a) the combination of sulforaphane, resveratrol and curcumin is administered at a therapeutically effective amount of about 0.05 mg to 0.3 mg/kg body weight of sulforaphane, about 2.5 mg to 10 mg/kg body weight of resveratrol, and about 2.5 mg to 10 mg/kg body weight of curcumin, including all values and ranges therebetween; and
b) the hypomethylating agent (HMA) is administered at a therapeutically effective amount ranging from about 0.2 mg/kg body weight to 12 mg/kg body weight, including all values and ranges therebetween.

In some embodiments of the above described method of treating hematological malignancy:
a) the combination of sulforaphane, resveratrol and curcumin is administered at a therapeutically effective amount of about 5 mg-30 mg of sulforaphane, about 250 mg-1000 mg of resveratrol, and about 250 mg-1000 mg of curcumin, including all values and ranges therebetween; and
b) the hypomethylating agent (HMA) is administered at a therapeutically effective amount ranging from about 0.2 mg/kg body weight to 12 mg/kg body weight, including all values and ranges therebetween.

In some embodiments of the above described method of treating hematological malignancy:
a) the combination of sulforaphane, resveratrol and curcumin is administered at a therapeutically effective amount ranging from 0.05 mg/kg body weight to 10 mg/kg body weight, including all values and ranges therebetween; and
b) azacitidine is administered at a therapeutically effective amount ranging from about 0.2 mg/kg body weight to 12 mg/kg body weight, including all values and ranges therebetween.

In some embodiments of the above described method of treating hematological malignancy:
a) the combination of sulforaphane, resveratrol and curcumin is administered at a therapeutically effective amount of about 0.05 mg to 0.3 mg/kg body weight of sulforaphane, about 2.5 mg to 10 mg/kg body weight of resveratrol, and about 2.5 mg to 10 mg/kg body weight of curcumin, including all values and ranges therebetween; and
b) azacitidine is administered at a therapeutically effective amount ranging from about 0.2 mg/kg body weight to 12 mg/kg body weight, including all values and ranges therebetween.

In some embodiments of the above described method of treating hematological malignancy:
a) the combination of sulforaphane, resveratrol and curcumin is administered at a therapeutically effective amount ranging from 0.05 mg/kg body weight to 10 mg/kg body weight, including all values and ranges therebetween; and
b) azacitidine is administered at a therapeutically effective amount of about 1.5 mg/kg body weight.

In some embodiments of the above described method of treating hematological malignancy:
a) the combination of sulforaphane, resveratrol and curcumin is administered at a therapeutically effective amount of about 0.05 mg to 0.3 mg/kg body weight of sulforaphane, about 2.5 mg to 10 mg/kg body weight of resveratrol, and about 2.5 mg to 10 mg/kg body weight of curcumin, including all values and ranges therebetween; and
b) azacitidine is administered at a therapeutically effective amount of about 1.5 mg/kg body weight.

In some embodiments of the above described method of treating hematological malignancy:
a) the combination of sulforaphane, resveratrol and curcumin is administered at a therapeutically effective amount ranging from 0.05 mg/kg body weight to 10 mg/kg body weight, including all values and ranges therebetween; and b) decitabine is administered at a therapeutically effective amount ranging from about 0.2 mg/kg body weight to 12 mg/kg body weight, including all values and ranges therebetween.

In some embodiments of the above described method of treating hematological malignancy:
- a) the combination of sulforaphane, resveratrol and curcumin is administered at a therapeutically effective amount of about 0.05 mg to 0.3 mg/kg body weight of sulforaphane, about 2.5 mg to 10 mg/kg body weight of resveratrol, and about 2.5 mg to 10 mg/kg body weight of curcumin, including all values and ranges therebetween; and
- b) decitabine is administered at a therapeutically effective amount ranging from about 0.2 mg/kg body weight to 12 mg/kg body weight, including all values and ranges therebetween.

In some embodiments of the above described method of treating hematological malignancy:
- a) the combination of sulforaphane, resveratrol and curcumin is administered at a therapeutically effective amount ranging from 0.05 mg/kg body weight to 10 mg/kg body weight, including all values and ranges therebetween; and
- b) decitabine is administered at a therapeutically effective amount of about 0.2 mg/kg body weight.

In some embodiments of the above described method of treating hematological malignancy:
- a) the combination of sulforaphane, resveratrol and curcumin is administered at a therapeutically effective amount of about 0.05 mg/kg to 0.3 mg/kg body weight of sulforaphane, about 2.5 mg/kg to 10 mg/kg body weight of resveratrol, and about 2.5 mg/kg to 10 mg/kg body weight of curcumin, including all values and ranges therebetween; and
- b) decitabine is administered at a therapeutically effective amount of about 1.5 mg/kg body weight.

In some embodiments of the above described methods of treating hematological malignancy or decreasing resistance to a hypomethylating agent (HMA), the combination of sulforaphane, resveratrol and curcumin is administered daily for 28 days (single cycle) alongside HMA (AZA or DEC therapy). In some embodiments, the therapeutic regimen comprises at least 1 cycle, such as 1 cycle, 2 cycles, 3 cycles, 4 cycles, 5 cycles, 6 cycles, 7 cycles, 8 cycles, 9 cycles, 10 cycles, or any number of cycles until remission (partial remission or complete remission) of MDS or AML is observed. In some embodiments, the therapeutic regimen comprises at least 4 cycles.

In some embodiments of the above described methods of treating hematological malignancy or decreasing resistance to a hypomethylating agent (HMA), the combination of sulforaphane, resveratrol and curcumin is administered alongside HMA therapy (AZA or DEC therapy) comprising 5+2+2 HMA dosages per cycle of 28 days, wherein one dose of the combination of sulforaphane, resveratrol and curcumin is administered prior to HMA administration and one dose the combination of sulforaphane, resveratrol and curcumin is administered after HMA administration. Thus, in such therapeutic regimen, a total of 11 dosages (or pills) is administered per cycle of 28 days. In some embodiments, said therapeutic regimen comprises at least 1 cycle, such as 1 cycle, 2 cycles, 3 cycles, 4 cycles, 5 cycles, 6 cycles, 7 cycles, 8 cycles, 9 cycles, 10 cycles, or any number of cycles until a remission (partial remission or complete remission) of MDS or AML is observed. In some embodiments, said therapeutic regimen comprises at least 4 cycles.

In some embodiments of the above described methods of treating hematological malignancy or decreasing resistance to AZA, the combination of sulforaphane, resveratrol and curcumin is administered alongside AZA therapy comprising 5+2+2 AZA dosages per cycle of 28 days, wherein one dose of the combination of sulforaphane, resveratrol and curcumin is administered prior to AZA administration and one dose the combination of sulforaphane, resveratrol and curcumin is administered after AZA administration. Thus, in such therapeutic regimen, a total of 11 dosages (or pills) is administered per cycle of 28 days. In some embodiments, said therapeutic regimen comprises at least 1 cycle, such as 1 cycle, 2 cycles, 3 cycles, 4 cycles, 5 cycles, 6 cycles, 7 cycles, 8 cycles, 9 cycles, 10 cycles, or any number of cycles until a remission (partial remission or complete remission) of MDS or AML is observed. In some embodiments, said therapeutic regimen comprises at least 4 cycles.

In some embodiments of the above described method of treating hematological malignancy, the method comprises administering: a) the combination comprising sulforaphane, resveratrol and curcumin, and b) the hypomethylating agent (HMA), to the subject orally or parenterally, or a combination of both oral and parenteral administration. In some embodiments, said method comprises administering the combination comprising sulforaphane, resveratrol and curcumin to the subject orally or parenterally, or a combination of both oral and parenteral administration. In some embodiments, said method comprises administering the hypomethylating agent (HMA) to the subject orally, parenterally or topically, or any combination thereof, for example, a combination of oral and parenteral administration or a combination of topical and parenteral administration.

In embodiments where the formulation of the combination comprising sulforaphane, resveratrol and curcumin (a single formulation or separate formulations of sulforaphane, resveratrol and curcumin) and the formulation of the hypomethylating agent (eg. azacitidine) are administered as separate formulations, all formulations can be administered using the same route of administration (e.g., orally or parenterally) or one formulation can be administered using one route of administration (e.g., orally or parenterally) and the other formulation(s) can be administered using the other routes of administration (e.g., if one is administered orally, the other is administered parenterally or vice versa).

In some embodiments, parenteral administration comprises administration via injection or infusion. In some embodiments, parenteral administration is selected from intraperitoneal, intravenous, intramuscular, intradermal, subcutaneous, intraosseal, intratumoral, intralesional and intrathecal administration. In some embodiments, parenteral administration is administration via intraperitoneal injection. In some embodiments, parenteral administration is via intravenous infusion.

In some embodiments, oral administration comprises administration via tablets, capsules, drops, mouth wash, mouth spray or any combinations thereof.

In some embodiments, topical administration comprises administration via creams, ointments, gels, gauze or in liquid form such as oils or tinctures, rectal or vaginal use such as suppositories, or any combinations thereof.

In some embodiments, parenteral administration comprises administration via injection or infusion. In some embodiments, parenteral administration is selected from intraperitoneal, intravenous, intramuscular, intradermal, subcutaneous, intraosseal, intratumoral, intralesional and intrathecal administration. In some embodiments, parenteral administration is administration via intraperitoneal injection. In some embodiments, parenteral administration is administration via intravenous infusion.

In some embodiments, the combination comprising sulforaphane, resveratrol and curcumin is formulated for oral administration. In some embodiments, the hypomethylating agent (HMA) is formulated for parenteral administration. In some embodiments, the azacitidine is formulated for intraperitoneal administration.

The single formulation or separate formulations as described herein can be any pharmaceutically acceptable dosage forms. In some embodiments, pharmaceutically acceptable dosage forms are selected from an oral dosage form or a parenteral dosage form. Oral dosage forms can be discrete units, such as hard or soft capsules, tablets, pills, or lozenges; or a liquid form such as emulsions, solutions, suspensions, syrups, and elixirs. Parenteral dosage forms can be a liquid form such as emulsions, solutions, and suspensions or a solid form packaged in a single-dose or multidose containers that is reconstituted prior to administration. In some embodiments, parenteral dosage form is a ready-to-use (RTU) liquid form.

In some embodiments of the above described method of treating hematological malignancy, the subject is a mammal. In some embodiments, the subject is a human.

In some embodiments of the above described method of treating hematological malignancy, the subject is a human patient who has developed resistance to treatment with hypomethylating agent (HMA). In some embodiments of the above described method of treating hematological malignancy, the subject is a human patient who has developed resistance to treatment with azacitidine.

In some embodiments of the above described method of treating hematological malignancy, the subject is a human patient who has developed resistance to treatment with hypomethylating agent (HMA). In some embodiments of the above described method of treating hematological malignancy, the subject is a human patient who has developed resistance to the treatment with azacitidine.

In some embodiments of the above described method of treating hematological malignancy, when the subject is a human patient who has developed resistance to the treatment with azacitidine, the method decreases or overcomes the azacitidine resistance and additionally improves/promotes the treatment of the hematological malignancy including MDS or AML.

In some embodiments of the above described method of treating hematological malignancy, the subject is a human patient who is sensitive to the treatment with hypomethylating agent (HMA). In some embodiments of the above described method of treating hematological malignancy, the subject is a human patient who is sensitive to the treatment with azacitidine.

In some embodiments of the above described method of treating hematological malignancy, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof.

In some embodiments of the above described method of treating hematological malignancy, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce side effects of the hypomethylating agent (HMA).

In some embodiments of the above described method of treating hematological malignancy, said method further comprises orally administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce side effects of the hypomethylating agent (HMA).

In some embodiments of the above described method of treating hematological malignancy selected from myelodysplastic syndrome (MDS) or acute myeloid leukemia (AML) in a subject in need thereof, said method comprises administering:
  a) a therapeutically effective amount of sulforaphane, resveratrol and curcumin;
  b) a therapeutically effective amount of a HMA selected from azacitidine (AZA), decitabine (DEC) and a combination thereof, and
  c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
  wherein c) is administered orally to reduce side effects of the hypomethylating agent (HMA).

In some embodiments of the above described method of treating hematological malignancy selected from myelodysplastic syndrome (MDS) or acute myeloid leukemia (AML) in a subject in need thereof, said method comprises administering:
  a) a therapeutically effective amount of sulforaphane, resveratrol and curcumin;
  b) a therapeutically effective amount of a HMA selected from azacitidine (AZA), decitabine (DEC) and a combination thereof, and
  c) a therapeutically effective amount of cannabidiol (CBD), cannabigerol (CBG), cannabinol (CBN), cannabidivarin (CBDV), cannabichromene (CBC) and tetrahydrocannabivarin (THCV),
  wherein c) is administered orally to reduce side effects of the hypomethylating agent (HMA).

In some embodiments of the above described method of treating hematological malignancy selected from MDS or AML in a subject in need thereof, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce the inflammatory response of the tissue to the hypomethylating agent (HMA).

In some embodiments of the above described method of treating hematological malignancy selected from MDS or AML in a subject in need thereof, said method further comprises topically administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce the inflammatory response of the tissue to the hypomethylating agent (HMA).

In some embodiments of the above described method of treating hematological malignancy selected from MDS or AML in a subject in need thereof, said method further comprises topically administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to the area of subcutaneous application of the HMA to reduce the inflammatory response of the tissue to the HMA.

In some embodiments of the above described method of treating hematological malignancy selected from myelodysplastic syndrome (MDS) or acute myeloid leukemia (AML) in a subject in need thereof, said method comprises administering:
- a) a therapeutically effective amount of sulforaphane, resveratrol and curcumin;
- b) a therapeutically effective amount of a HMA selected from azacitidine (AZA), decitabine (DEC) and a combination thereof, and
- c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
- wherein c) is administered topically to the area of subcutaneous application of the hypomethylating agent (HMA) to reduce the inflammatory response of the tissue to the hypomethylating agent (HMA).

In some embodiments of the above described method of treating hematological malignancy selected from myelodysplastic syndrome (MDS) or acute myeloid leukemia (AML) in a subject in need thereof, said method comprises administering:
- a) a therapeutically effective amount of sulforaphane, resveratrol and curcumin;
- b) a therapeutically effective amount of a HMA selected from azacitidine (AZA), decitabine (DEC) and a combination thereof, and
- c) a therapeutically effective amount of cannabidiol (CBD), cannabigerol (CBG), cannabinol (CBN), cannabidivarin (CBDV), cannabichromene (CBC) and tetrahydrocannabivarin (THCV),
- wherein c) is administered topically to the area of subcutaneous application of the hypomethylating agent (HMA) to reduce the inflammatory response of the tissue to the hypomethylating agent (HMA).

In some embodiments of the above described method of treating hematological malignancy, said method further comprises administering a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, to reduce side effects of the HMA or to reduce the inflammatory response of the tissue to the HMA.

In some embodiments of the above described method of treating hematological malignancy selected from myelodysplastic syndrome (MDS) or acute myeloid leukemia (AML) in a subject in need thereof, said method comprises administering:
- a) a therapeutically effective amount of sulforaphane, resveratrol and curcumin;
- b) a therapeutically effective amount of a HMA selected from azacitidine (AZA), decitabine (DEC) and a combination thereof, and
- c) a therapeutically effective amount of cannabidiol (CBD), cannabigerol (CBG), cannabinol (CBN), cannabidivarin (CBDV), cannabichromene (CBC) and tetrahydrocannabivarin (THCV), wherein c) is:
- i) administered orally to reduce side effects of the HMA, or
- ii) administered topically to the area of subcutaneous application of the HMA to reduce the inflammatory response of the tissue to the HMA, or
- iii) administered both orally and topically according to i) and ii).

The present disclosure also relates to a combination comprising:
- a) a therapeutically effective amount of hypomethylating agent (HMA) selected from azacitidine (AZA), decitabine (DEC), or a combination thereof; and
- b) a therapeutically effective amount of sulforaphane, resveratrol and curcumin, for use as a medicament.

In some embodiments, the present disclosure provides a combination comprising:
- a) a therapeutically effective amount of azacitidine (AZA); and
- b) a therapeutically effective amount of sulforaphane, resveratrol and curcumin, for use as a medicament.

In some embodiments, the present disclosure provides a combination comprising:
- a) a therapeutically effective amount of decitabine (DEC); and
- b) a therapeutically effective amount of sulforaphane, resveratrol and curcumin, for use as a medicament.

In some embodiments, the present disclosure provides a combination comprising:
- a) a therapeutically effective amount of hypomethylating agent (HMA) selected from azacitidine (AZA), decitabine (DEC), or a combination thereof;
- b) a therapeutically effective amount of sulforaphane, resveratrol and curcumin, and
- c) optionally, a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, for use as a medicament.

In some embodiments, the present disclosure provides a combination comprising:
- a) a therapeutically effective amount of hypomethylating agent (HMA) selected from azacitidine (AZA), decitabine (DEC), or a combination thereof;
- b) a therapeutically effective amount of sulforaphane, resveratrol and curcumin, and
- c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, for use as a medicament.

The present disclosure further provides a combination comprising:
- a) a therapeutically effective amount of hypomethylating agent (HMA) selected from azacitidine (AZA), decitabine (DEC), and a combination thereof; and
- b) a therapeutically effective amount of sulforaphane, resveratrol and curcumin, for use in the treatment of myelodysplastic syndrome (MDS) or acute myeloid leukemia (AML).

In some embodiments, the present disclosure provides a combination comprising:
- a) a therapeutically effective amount of azacitidine (AZA); and
- b) a therapeutically effective amount of sulforaphane, resveratrol and curcumin, for use in the treatment of acute myeloid leukemia (AML).

In some embodiments, the present disclosure provides a combination comprising:
a) a therapeutically effective amount of azacitidine (AZA); and
b) a therapeutically effective amount of sulforaphane, resveratrol and curcumin, for use in the treatment of myelodysplastic syndrome (MDS).

In some embodiments, the present disclosure provides a combination comprising:
a) a therapeutically effective amount of decitabine (DEC); and
b) a therapeutically effective amount of sulforaphane, resveratrol and curcumin, for use in the treatment of myelodysplastic syndrome (MDS) or acute myeloid leukemia (AML).

In some embodiments, the present disclosure provides a combination comprising:
a) a therapeutically effective amount of hypomethylating agent (HMA) selected from azacitidine (AZA), decitabine (DEC), or a combination thereof;
b) a therapeutically effective amount of sulforaphane, resveratrol and curcumin, and
c) optionally, a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, for use in the treatment of myelodysplastic syndrome (MDS) or acute myeloid leukemia (AML).

In some embodiments, the present disclosure provides a combination comprising:
a) a therapeutically effective amount of hypomethylating agent (HMA) selected from azacitidine (AZA), decitabine (DEC), or a combination thereof;
b) a therapeutically effective amount of sulforaphane, resveratrol and curcumin, and
c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof, for use in the treatment of myelodysplastic syndrome (MDS) or acute myeloid leukemia (AML).

In embodiments concerning combination for use as discussed above, ALL the additional features of said combination/use; or the corresponding combination comprising sulforaphane, resveratrol and curcumin, and the hypomethylating agent (HMA) are already defined in the above embodiments relating to the method of decreasing resistance to a hypomethylating agent, or the method of treating a hematological malignancy, which is INCORPORATED HEREIN IN ITS ENTIRETY.

The present disclosure also relates to a pharmaceutical kit or package comprising:
a) a therapeutically effective amount of a combination essentially consisting of sulforaphane, resveratrol and curcumin;
b) optionally, a therapeutically effective amount of hypomethylating agent (HMA) selected from azacitidine (AZA), decitabine (DEC), or a combination thereof; and
c) an instruction manual containing instructions for using a) and b).

In some embodiments, the present disclosure provides a pharmaceutical kit or package comprising:
a) a therapeutically effective amount of hypomethylating agent (HMA) selected from azacitidine (AZA), decitabine (DEC), or a combination thereof;
b) a therapeutically effective amount of sulforaphane, resveratrol and curcumin; and
c) an instruction manual containing instructions for using a) and b),
wherein both a) and b) are formulated as oral dosage forms.

In some embodiments, the present disclosure provides a pharmaceutical kit or package comprising:
a) a therapeutically effective amount of hypomethylating agent (HMA) selected from azacitidine (AZA), decitabine (DEC), or a combination thereof;
b) a therapeutically effective amount of sulforaphane, resveratrol and curcumin; and
c) an instruction manual containing instructions for using a) and b),
wherein both a) and b) are administered orally.

In some embodiments of the pharmaceutical kit or package, said kit or package comprises:
a) a therapeutically effective amount of a combination essentially consisting of sulforaphane, resveratrol and curcumin;
b) optionally, a therapeutically effective amount of azacitidine (AZA); and
c) an instruction manual containing instructions for using a) and b).

In some embodiments of the pharmaceutical kit or package, said kit or package comprises:
a) a therapeutically effective amount of a combination essentially consisting of sulforaphane, resveratrol and curcumin;
b) a therapeutically effective amount of azacitidine (AZA); and
c) an instruction manual containing instructions for using a) and b).

In some embodiments of the pharmaceutical kit or package, the kit or package comprises:
a) a therapeutically effective amount of a combination essentially consisting of sulforaphane, resveratrol and curcumin;
b) optionally, a therapeutically effective amount of hypomethylating agent (HMA) selected from azacitidine (AZA), decitabine (DEC), or a combination thereof; and
c) an instruction manual containing instructions for using a) and b),
for use in treating hematological malignancy, or decreasing resistance to the hypomethylating agent (HMA) caused by treatment of hematological malignancy, wherein the hematological malignancy is myelodysplastic syndrome (MDS) or acute myeloid leukemia (AML).

In some embodiments of the pharmaceutical kit or package, the kit or package is used in the treatment of hematological malignancy in a subject in need thereof.

In some embodiments of the pharmaceutical kit or package, the kit or package is used in the treatment of AML in a subject in need thereof.

In some embodiments of the pharmaceutical kit or package, the kit or package is used in the treatment of MDS in a subject in need thereof.

In some embodiments of the pharmaceutical kit or package, the kit or package is used for decreasing resistance to the hypomethylating agent (HMA) caused by treatment of hematological malignancy.

In some embodiments of the pharmaceutical kit or package, the kit or package is used for decreasing resistance to azacitidine caused by treatment of AML.

In some embodiments of the pharmaceutical kit or package, the kit or package is used for decreasing resistance to azacitidine caused by treatment of MDS.

In some embodiments of the pharmaceutical kit or package, the kit or package comprises:
- a) a therapeutically effective amount of a combination essentially consisting of sulforaphane, resveratrol and curcumin;
- b) optionally, a therapeutically effective amount of azacitidine (AZA); and
- c) an instruction manual containing instructions for using a) and b),
- for use in treating hematological malignancy selected from myelodysplastic syndrome (MDS) and acute myeloid leukemia (AML).

In some embodiments of the pharmaceutical kit or package, the kit or package comprises:
- a) a therapeutically effective amount of a combination essentially consisting of sulforaphane, resveratrol and curcumin;
- b) optionally, a therapeutically effective amount of azacitidine (AZA); and
- c) an instruction manual containing instructions for using a) and b),
- for use in decreasing resistance to azacitidine caused during the treatment of hematological malignancy selected from myelodysplastic syndrome (MDS) and acute myeloid leukemia (AML).

In some embodiments, the present disclosure provides a pharmaceutical kit or package comprising:
- a) a therapeutically effective amount of a combination essentially consisting of sulforaphane, resveratrol and curcumin;
- b) optionally, a therapeutically effective amount of hypomethylating agent (HMA) selected from azacitidine (AZA), decitabine (DEC), or a combination thereof;
- c) optionally, a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof; and
- d) an instruction manual containing instructions for using a), b) and c).

In some embodiments, the present disclosure provides a pharmaceutical kit or package comprising:
- a) a therapeutically effective amount of a combination essentially consisting of sulforaphane, resveratrol and curcumin;
- b) a therapeutically effective amount of hypomethylating agent (HMA) selected from azacitidine (AZA), decitabine (DEC), or a combination thereof;
- c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof; and
- d) an instruction manual containing instructions for using a), b) and c).

In some embodiments, the present disclosure also provides a combination or a pharmaceutical kit or package comprising:
- a) a therapeutically effective amount of sulforaphane, resveratrol and curcumin;
- b) a therapeutically effective amount of a hypomethylating agent (HMA) selected from azacitidine (AZA), decitabine (DEC) and a combination thereof, and
- c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
- to reduce side effects of the HMA during treatment of myelodysplastic syndrome (MDS) or acute myeloid leukemia (AML).

In some embodiments, the present disclosure also provides a combination or a pharmaceutical kit or package comprising:
- a) a therapeutically effective amount of sulforaphane, resveratrol and curcumin;
- b) a therapeutically effective amount of a hypomethylating agent (HMA) selected from azacitidine (AZA), decitabine (DEC) and a combination thereof, and
- c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
- wherein c) is administered orally to reduce side effects of the HMA during treatment of myelodysplastic syndrome (MDS) or acute myeloid leukemia (AML).

In some embodiments, the present disclosure also provides a combination or a pharmaceutical kit or package comprising:
- a) a therapeutically effective amount of sulforaphane, resveratrol and curcumin;
- b) a therapeutically effective amount of a hypomethylating agent (HMA) selected from azacitidine (AZA), decitabine (DEC) and a combination thereof, and
- c) a therapeutically effective amount of cannabidiol (CBD), cannabigerol (CBG), cannabinol (CBN), cannabidivarin (CBDV), cannabichromene (CBC) and tetrahydrocannabivarin (THCV), wherein c) is administered orally to reduce side effects of the HMA during treatment of myelodysplastic syndrome (MDS) or acute myeloid leukemia (AML).

In some embodiments, the present disclosure also provides a combination or a pharmaceutical kit or package comprising:
- a) a therapeutically effective amount of sulforaphane, resveratrol and curcumin;
- b) a therapeutically effective amount of a hypomethylating agent (HMA) selected from azacitidine (AZA), decitabine (DEC) and a combination thereof, and
- c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
- to reduce the inflammatory response of the tissue to the HMA during treatment of myelodysplastic syndrome (MDS) or acute myeloid leukemia (AML).

In some embodiments, the present disclosure also provides a combination or a pharmaceutical kit or package comprising:

a) a therapeutically effective amount of sulforaphane, resveratrol and curcumin;
b) a therapeutically effective amount of a hypomethylating agent (HMA) selected from azacitidine (AZA), decitabine (DEC) and a combination thereof, and
c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
wherein c) is administered topically to reduce the inflammatory response of the tissue to the HMA during treatment of myelodysplastic syndrome (MDS) or acute myeloid leukemia (AML).

In some embodiments, the present disclosure also provides a combination or a pharmaceutical kit or package comprising:
a) a therapeutically effective amount of sulforaphane, resveratrol and curcumin;
b) a therapeutically effective amount of a hypomethylating agent (HMA) selected from azacitidine (AZA), decitabine (DEC) and a combination thereof, and
c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
wherein c) is administered topically to the area of subcutaneous application of the HMA to reduce the inflammatory response of the tissue to the HMA during treatment of myelodysplastic syndrome (MDS) or acute myeloid leukemia (AML).

In some embodiments, the present disclosure also provides a combination or a pharmaceutical kit or package comprising:
a) a therapeutically effective amount of sulforaphane, resveratrol and curcumin;
b) a therapeutically effective amount of a hypomethylating agent (HMA) selected from azacitidine (AZA), decitabine (DEC) and a combination thereof, and
c) a therapeutically effective amount of cannabidiol (CBD), cannabigerol (CBG), cannabinol (CBN), cannabidivarin (CBDV), cannabichromene (CBC) and tetrahydrocannabivarin (THCV),
wherein c) is administered topically to the area of subcutaneous application of the HMA to reduce the inflammatory response of the tissue to the HMA during treatment of myelodysplastic syndrome (MDS) or acute myeloid leukemia (AML).

In some embodiments, the present disclosure also provides a combination or a pharmaceutical kit or package comprising:
a) a therapeutically effective amount of sulforaphane, resveratrol and curcumin;
b) a therapeutically effective amount of a HMA selected from azacitidine (AZA), decitabine (DEC) and a combination thereof, and
c) a therapeutically effective amount of at least one of cannabidiol (CBD), cannabigerol (CBG), cannabinol (CBN), cannabidivarin (CBDV), cannabichromene (CBC), tetrahydrocannabivarin (THCV) or any combination thereof,
wherein c) is:
i) administered orally to reduce side effects of the HMA, or
ii) administered topically to the area of subcutaneous application of the HMA to reduce the inflammatory response of the tissue to the HMA, or
iii) administered both orally and topically according to i) and ii).

In some embodiments, the present disclosure also provides a combination or a pharmaceutical kit or package comprising:
a) a therapeutically effective amount of sulforaphane, resveratrol and curcumin;
b) a therapeutically effective amount of a HMA selected from azacitidine (AZA), decitabine (DEC) and a combination thereof, and
c) a therapeutically effective amount of cannabidiol (CBD), cannabigerol (CBG), cannabinol (CBN), cannabidivarin (CBDV), cannabichromene (CBC) and tetrahydrocannabivarin (THCV),
wherein c) is:
i) administered orally to reduce side effects of the HMA, or
ii) administered topically to the area of subcutaneous application of the HMA to reduce the inflammatory response of the tissue to the HMA, or
iii) administered both orally and topically according to i) and ii).

In embodiments concerning a pharmaceutical kit or package as discussed above, ALL the additional features of said kit; or the corresponding combination comprising sulforaphane, resveratrol and curcumin, and the hypomethylating agent (HMA) are already defined in the above embodiments relating to the method of decreasing resistance to a hypomethylating agent, or the method of treating a hematological malignancy, which is INCORPORATED HEREIN IN ITS ENTIRETY.

Thus, the present disclosure particularly aims at a combination therapy primarily involving: a) a combination of sulforaphane, resveratrol and curcumin, and b) a hypomethylating agent (HMA) selected from azacitidine (AZA) and decitabine (DEC), in achieving the desired technical effects including but not limiting to improved/synergistic treatment of myelodysplastic syndrome (MDS) or acute myeloid leukemia (AML) and/or decreasing or overcoming resistance to hypomethylating agent such as azacitidine or decitabine in a subject in need thereof.

The myelodysplastic syndromes (MDS) are a group of clonal hematopoietic malignancies/cancers involving altered differentiation of blood cells and leading to cytopenias (eg. anemia, neutropenia, thrombocytopenia etc.) that can further progress to acute myeloid leukemia (AML). Said AML is therefore a severe manifestation of MDS and is a cancer of the myeloid line of blood cells characterized by the rapid growth of abnormal cells that build up in the bone marrow and blood and interfere with normal blood cell production. In some embodiments, the hematological malignancy including MDS or AML treated according to the methods of the present disclosure is of any status or stage, as long as a person skilled in the art or a medical practitioner deems administration of the combination therapy of the present disclosure fit and/or necessary for treatment of such malignancy.

As the present disclosure provides a combination therapy comprising administering: a) a combination of sulforaphane, resveratrol and curcumin, and b) azacitidine and/or decitabine; it would be understood that the amounts/dosing regimen disclosed herein for said a) is combined with the dosing regimen disclosed herein for said b).

The combination therapy of the present disclosure comprising: a) a combination of sulforaphane, resveratrol and curcumin, and b) azacitidine and/or decitabine is cytotoxic to cancer cells in MDS and AML. In some embodiments, the level of cytotoxicity exhibited by the combination therapy is statistically significantly more than that exhibited by said a) or b) alone. In some embodiments, the combination therapy comprising said a) and b) shows a synergistic effect against cancer cells MDS or AML compared to the sum of effects shown by a) and b) alone.

In some embodiments, practicing the combination therapy disclosed herein comprising: a) a combination of sulforaphane, resveratrol and curcumin, and b) a hypomethylating agent (HMA) selected from azacitidine (AZA) and decitabine (DEC), provides about 5%, 10%, 15%, 20%, 25%, 30%, 35%, 40%, 45%, 50%, 55%, 60%, 65%, 70%, 80%, 90% or 100%, including values and ranges therebetween, reduction in the number of cancer cells in MDS or AML compared to the number of cancer cells prior to practicing the combination therapy.

In some embodiments, practicing the combination therapy disclosed herein comprising: a) a combination of sulforaphane, resveratrol and curcumin, and b) a hypomethylating agent (HMA) selected from azacitidine (AZA) and decitabine (DEC), provides about 2.5-fold, 3-fold, 4-fold, 5-fold, 7.5-fold, 8-fold, 10-fold, 12-fold, 15-fold, 20-fold, 25-fold, 30-fold, 35-fold, 40-fold, 45-fold, 50-fold, 55-fold, 60-fold, 65-fold, 70-fold, 80-fold, or 90-fold, including values and ranges therebetween, reduction in the number of cancer cells in MDS or AML compared to the number of cancer cells prior to practicing the combination therapy.

Sulforaphane (1-isothiocyanato-4-methylsulfinyl butane)

Sulforaphane is an isothiocyanate derived from plants. It is mainly found in cruciferous vegetables such as but not limited to broccoli (*Brassica oleracea* var. *Italica*) and its sprouts, kohlrabi (*Brassica oleracea* Gongylodes Group), cauliflower (*Brassica oleracea* var. *botrytis*), cabbage (*Brassica oleracea* var. *capitata*), bok Choy (*Brassica rapa* subsp. *Chinensis*), kale (*Brassica oleracea* var. *sabellica*), mustard (*Brassica nigra*), turnip (*Brassica rapa* subsp. *rapa*) and radish (*Raphanus raphanistrum*). Sulforaphane usually exerts anti-cancer effects by induction of carcinogen defense enzymes, inhibition of carcinogen-activating enzymes, induction of DNA repair and cell cycle arrest, inhibition of angiogenesis and metastasis, and antioxidant or anti-inflammatory effects.

Resveratrol (5-[(E)-2-(4-hydroxyphenyl)ethenyl]benzene-1, 3-diol)

Resveratrol is a polyphenolic compound that exists as cis- and trans-stereoisomers. Trans-resveratrol appears to be the primary active form. The major sources of resveratrol are including but not limiting to grapes (*Vitis vinifera*), blueberries (*Vaccinium angustifolium*), cranberries (*Vaccinium macrocarpon*) and peanuts (*Arachis hypogaea*). Trans-resveratrol exerts its antimutagenic activity by induction of anti-inflammatory, anti-angiogenic, apoptotic and antioxidant activity.

Curcumin: (1E,6E)-1,7-bis(4-hydroxy-3-m ethoxyphenyl) hepta-1,6-diene-3,5-dione)

Curcumin is one of the key active ingredients of turmeric (*Curcuma longa*) which is known to modulate cell cycle, nuclear factor kappa B subunit 1 (NFKB1), WNT/beta-catenin, PI3K-AKT1 signalling, epigenetics regulation like DNA CpG methylation and histone acetylation and apoptotic signalling pathways. Curcumin exerts anti-cancer effects by its antioxidant, anti-inflammatory and anti-angiogenic activities.

Azacitidine and Decitabine

Azacitidine and its deoxy derivative decitabine (5-aza-2'deoxycytidine) are both analogs of cytidine in which the carbon atom at position 5 in the pyrimidine ring is replaced by a nitrogen atom. Metabolism of azacitidine and decitabine are similar as they both get converted to their triphosphates.

Decitabine triphosphate gets incorporated only into DNA. Azacitidine once converted to azacitidine triphosphate, is incorporated into the RNA. A smaller portion of azacitidine, about 10% to 20%, is converted to 5-aza-2'-deoxycytidine triphosphate via the enzyme ribonucleotide reductase and is available for incorporation into the DNA. Incorporation into the DNA results in the formation of adducts between the DNA and DNMT-1 [DNA (cytosine-5)-methyltransferase 1].

The present inventors have developed the combination therapy described herein, primarily for augmenting chemotherapy in MDS or AML patients to achieve synergistic treatment results as well as to decrease or overcome the azacitidine/decitabine resistance in patients who suffer from MDS or AML but have acquired resistance to azacitidine/decitabine. The inventors through their efforts, incorporated all the genomic aberrations with their prevalence in cancer to come up with a pathway characteristic map and their dominance score. The pathway characteristic map encompasses all the relevant pathways for cancer indication. Further, the relevant therapy/drug (eg. azacitidine) supporting or interfering pathways were listed. In the next step, the overlap between the indication pathway characteristics and drug (eg. azacitidine) supporting or interfering pathways lead to a list of pathways that can be targeted based on plant-based compounds. By using advanced mathematical algorithms, the inventors were able to scientifically match the right set of plant based compounds to add-on/combine with the relevant drug (eg. azacitidine) for MDS or AML. Using this approach, all the related pathways for a drug (eg. azacitidine) based on their relevance to the indication (MDS and AML) were targeted by a combination of plant derived compounds thereby providing a holistic approach to deal with drug resistance (eg. azacitidine) as well as improving the treatment of MDS and AML.

Figure 1:
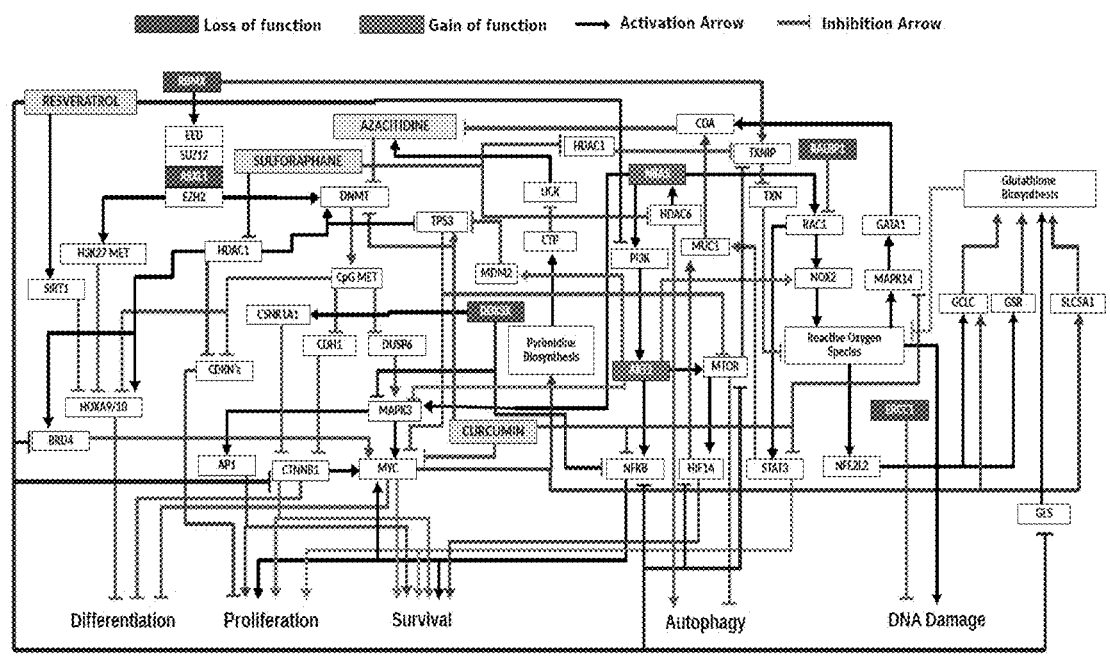
FIG. 1 illustrates cancer pathway network showing genomic aberrations within cancer pathways and the rationale behind the synergistic effect of the combination of sulforaphane, resveratrol, and curcumin with azacitidine in OCI-M2 cell-line.
Figure 2:
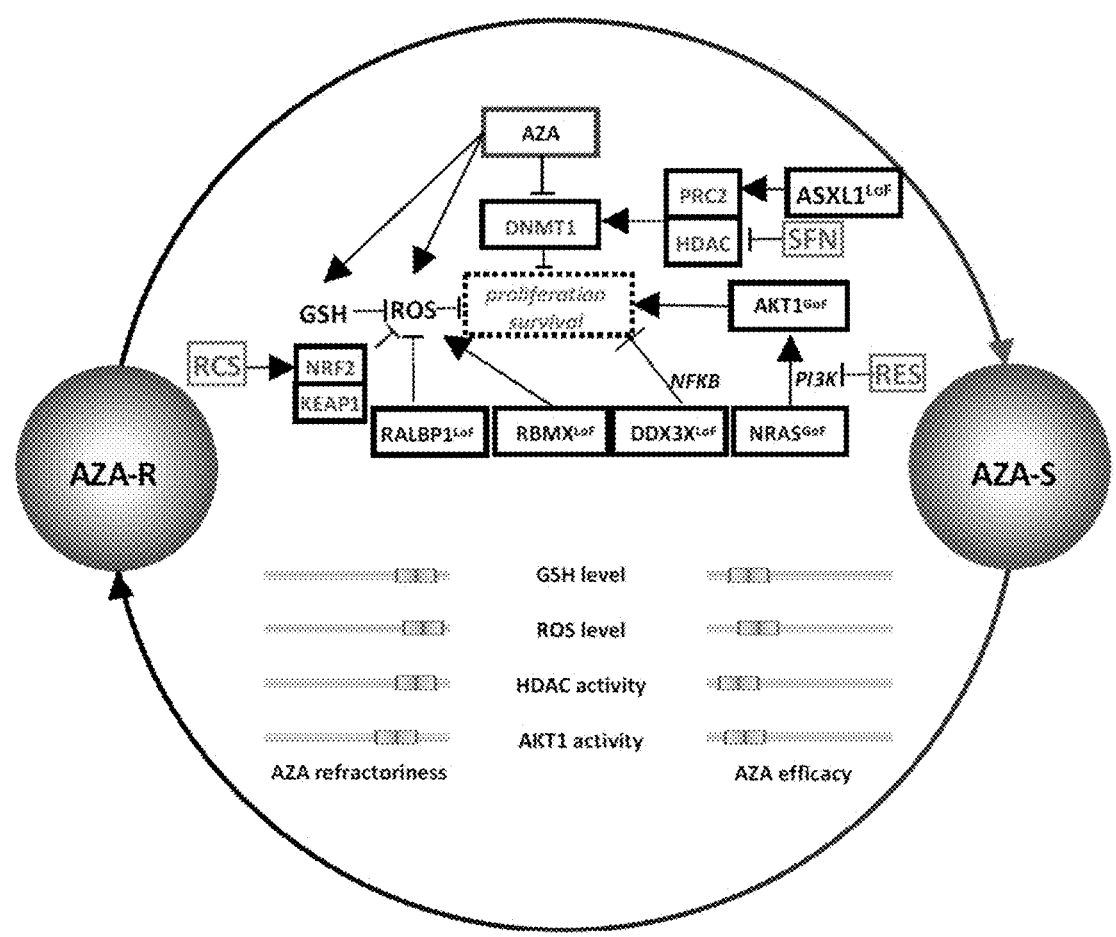
FIG. 2 illustrates a graphical representation of AZA-R [azacitidine-resistant] and AZA-S [azacitidine-sensitive] states that can be distinguished by several levels of molecular environment dependent on mutation status of genes and pathways.

In an embodiment, the cancer pathway network diagram showing genomic aberrations within cancer pathways and the rationale behind the synergistic effect of the combination of sulforaphane, resveratrol and curcumin with a hypomethylating drug such as azacitidine is shown in FIG. 1. Through the extensive analysis summarized above, the present inventors identified the plant based compounds: Sulforaphane, Resveratrol and Curcumin. Each of these agents impact albeit differently the metabolic pathways involving both GSH and ROS, as well as the PI3K/AKT1 pro-survival pathway. GSH pathways is inhibited by the combination of Sulforaphane, Resveratrol and Curcumin, thereby re-sensitizing AZA-R cell. Sulforaphane inhibits HDAC pathways which result in the downregulation of HOXA (HOXA9), MYC, AKT1, ERK, autophagy and anti-oxidant signalling pathways. Resveratrol activates SIRT1 which inhibits HOXA9/10 signalling. It also inhibits PI3K-AKT-MTOR, hypoxia (HIF1), GSH biosynthesis (GLS), WNT-CTNNB1 and BRD4-MYC signalling. Curcumin inhibits WNT-CTNNB1, NFKB, ERK, survival signalling pathways and activates TP53 signalling. Additionally, Sulforaphane and Curcumin also inhibit DNA CpG methylation which amplifies the AZA impact.

Resistance to HMA therapy is a major unmet need in treating patients with MDS and AML. Based on the above extensive analysis summarized above, the present inventors thus identified Sulforaphane, Resveratrol and Curcumin as three agents capable of correcting the perturbed pathways/metabolism in cancerous cells of MDS and AML. Said combination of Sulforaphane, Resveratrol and Curcumin was shown to re-sensitize HMA resistant cells such as AZA-resistant cells to AZA-sensitive, as also demonstrated in the Examples below.

While the present combination therapy disclosed herein can be employed in any patient suffering from MDS or AML, and works synergistically to improve the treatment as well as decreasing or overcoming drug resistance (eg. azacitidine) in patients, the present inventors additionally arrived at certain molecular level observations in some cells during the present study/analysis which could further help understand the correlation of gene aberrations and the effect of sulforaphane, resveratrol and curcumin combination along with HMA (eg. azacitidine) in cancerous cells of MDS/AML. Particularly, a study on more specific understanding of molecular defects in HMA-resistant disease was undertaken to further aid in designing the present therapeutic interventions. Accordingly, the present inventors designed an experimental system to examine HMA resistance and screen for candidate treatments to decrease or reverse the resistance. In-vitro models of azacitidine (AZA)-resistant OCI-M2 cells and AZA-sensitive OCI-M2 cells were generated to study genetic and epigenetic defects during the acquisition of AZA resistance. More specifically, the inventors constructed a cellular model of AZA resistance starting with MDS-derived AML cells from OCI-M2 cell line (DSMZ) that were sensitive to AZA (AZA-S). After chronic concentration exposure to AZA, the inventors selected subclones (N=6) whose inhibition concentration of AZA with 50% effect on cell viability (IC50, using WST-1 assay) was 3 logs higher compared to AZA-S cells and these cells were designated as AZA-R. Gene aberrations in two additional MDS/AML cell lines-SKM1 and MOLM13 were also studied. Based on the extensive analysis/results, it was found that the sulforaphane, resveratrol and curcumin combination was more sensitive in augmenting the affect of HMA (eg. azacitidine) in cancerous cells having genomic aberration in at least one gene selected from tet methylcytosine dioxygenase 2 (TET2) and ASXL transcriptional regulator 1 (ASXL1). More particularly, while all cell types were effective with the sulforaphane, resveratrol and curcumin combination along with azacitidine, AZA-R OCI-M2 cells, AZA-S OCI-M2 cells and SKM1 cells possessing mutations in TET2 and ASXL1 were even more effective in treating the hematological malignancy (MDS and AML) and/or overcoming the resistance to azacitidine. Hypomethylating agents are known to inhibit DNA CpG methylation and one of the reasons for resistance is through glutathione pathway. ASXL1 and TET2 mutations whether alone or in combination impact DNA methylation and in turn impacts Glutathione (GSH) therefore cells possessing mutations in ASXL1 and TET2 were even more effective in treating the hematological malignancy (MDS and AML) and/or overcoming the resistance to azacitidine. These results additionally show that the efficacy of the presently described combination of sulforaphane, resveratrol and curcumin along with azacitidine in treating MDS/AML further enhances in the presence of genomic aberration(s) in at least one gene selected from tet methylcytosine dioxygenase 2 (TET2) and ASXL transcriptional regulator 1 (ASXL1).

Accordingly, the present disclosure provides a two-pronged approach for overcoming HMA (eg. azacitidine) resistance and improving treatment of MDS or AML, wherein:
1) Patients or cancer cells irrespective of their genomic profile when treated with combination of sulforaphane, resveratrol and curcumin along with azacitidine or decitabine were more effective in decreasing/overcoming azacitidine or decitabine resistance and improving MDS/AML treatment; and
2) A further/additional enhancement of said decreased azacitidine or decitabine resistance and improved MDS/AML treatment is observed when patients or cancer cells possess genomic aberrations in at least one gene selected from TET2 and ASXL1 and are treated with a combination of sulforaphane, resveratrol and curcumin along with azacitidine or decitabine.

Thus, regardless of the genomic profile, the combination therapy of sulforaphane, resveratrol and curcumin along with azacitidine works well to overcome HMA (eg. azacitidine) induced resistance as well as improves the overall treatment of MDS or AML.

Additionally, since cancer physiology is a diverse and ever emerging research area, the present combination therapy according to the present disclosure is specifically applicable for treating MDS or AML only, and may not be applicable/useful in treating other cancer types and/or in cancer treatments employing different chemotherapeutic agents.

It is to be understood that the foregoing descriptive matter is illustrative of the disclosure and not a limitation. While considerable emphasis has been placed herein on the particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein. Similarly, additional embodiments and features of the present disclosure will be apparent to one of ordinary skill in art based upon description provided herein.

Descriptions of well-known/conventional methods/steps and techniques are omitted so as to not unnecessarily obscure the embodiments herein. Further, the disclosure herein provides for examples illustrating the above-described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

As regards all the embodiments defined/characterized in this specification, it is intended that each embodiment can be combined with one or more other embodiments as described herein. As an example, if a method recites 3 alternate embodiments A, B and C, it is to be understood that the specification unambiguously discloses embodiments corresponding to combinations: A, B; B, C; C, A; and A, B, C, unless specifically mentioned otherwise. If a medical use aspect recites 3 alternate embodiments A, B and C, it is to be understood that the specification unambiguously discloses embodiments corresponding to combinations: A, B; B, C; C, A; and A, B, C, unless specifically mentioned otherwise. If a product (eg. a combination product) recites 3 alternate embodiments A, B and C, it is to be understood that the specification unambiguously discloses embodiments corresponding to combinations: A, B; B, C; C, A; and A, B, C, unless specifically mentioned otherwise. Similarly, also in those cases where embodiments do not recite alternatives, it is understood that any combination of subject-matter covered thereby is considered to be explicitly disclosed. The above considerations apply mutatis mutandis to all embodiments of the present specification.

INCORPORATION BY REFERENCE

All references, articles, publications, patents, patent publications, and patent applications (if any) cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

Example 1: Cytotoxicity Assay on AZA-S and AZA-R Cells

Cell viability was analyzed on AZA-S & AZA-R cells using colorimetric assay (WST-1 assay). OCI-M2 cell line that was established from a 56-year-old patient with erythroleukemia (AML-M6) and representing the end stage of a previously identified myelodysplastic syndrome was used. Said OCI-M2 cell line was obtained from DSMZ collection (Braunschweich, Germany, #ACC 619). Since OCI-M2 cell line has been used for the study of key pathways involved in AML, this serves as a good model for understanding the intricacies of AML and attain a therapeutic solution.

A strategy of producing azacitidine-resistant (AZA-R) OCI-M2 subclones (#1,3,16,20,33,34) from azacitidine-sensitive (AZA-S) OCI-M2 cells was employed by culturing the AZA-S OCI-M2 cells in about 8 µM azacitidine added to media every 2 days for a period of about 6 weeks. WST-1 reagent to assess cell proliferation was obtained from Roche (Basel, Switzerland). Assay was performed on the AZA-S and AZA-R OCIM2 cells in presence and absence of azacitidine and/or additional substances. AZA-R #1, AZA-R #20, AZA-R #33, AZA-R #34 are AZA-R clones that were selected based on the screening using AZA-S cells treated with high doses of AZA.

FIG. 3 demonstrates the results of cell viability and proliferation of OCI-M2 AZA-S and AZA-R cells. The results demonstrate that providing azacitidine did not have a positive effect on AZA-R cells whereas AZA-S cells showed lower cell viability when treated with azacitidine. Particularly, FIG. 3A demonstrates that AZA is sensitive in AZA-S cell-line and resistant in AZA-R cell-line. FIG. 3B simply shows the proliferation results of all cells i.e. AZA-S and AZA-R variants #1, #20, #33, #34. Said FIG. 3B illustrates that both AZA-S and AZA-R cells were active in proliferation. The difference in the rate of proliferation of AZA-S vs. AZA-R variants is insignificant.

Example 2: Effect of the Combination of Sulforaphane, Resveratrol and Curcumin on Azacitidine Sensitivity in OCI-M2 AZA-S and AZA-R Cells OCI-M2 cells were purchased from DSMZ (Braunschweich, Germany) and cultured according to manufacturer recommendations with IMDM culture medium (Gibco, Thermo Fisher Scientific, Waltham, Mass., USA) enriched with 20% FBS (Biosera, Nuaille, France) and 1% Penicilline-Streptomycine (Sigma, St. Louis, Mo., USA). Azacitidine-resistant OCI-M2 cells were created by treating single-cell sorted culture by sublethal doses of azacitidine 3 times a week. WST-1 reagent to assess cell proliferation was obtained from Roche (Basel, Switzerland). WST-1 assay was performed for AZA-S and AZA-R OCI-M2 cell lines after seeding 10000 cells per well on 96-well flat bottom plate (VWR, Randor, Pa., USA) after 72-hours incubation in the presence of plant supplements (sulforaphane, resveratrol and curcumin at 5 µL each) and azacitidine (0.01 µM to 100 µM) in different combinations as shown in FIGS. 4 and 5, respectively. Vehicle treated cells were used as control. The plant supplements sulforaphane, resveratrol and curcumin were purchased from Selleckchem (Munich, Germany). The genomic sample from the cell line was obtained using the NucleoSpin Tissue DNA purification kit (Duren, Germany). The samples were analyzed by cytogenetics including Fluorescence in situ hybridization (FISH) and mutations were detected via NGS TruSight Myeloid 54-MDS gene panel (Illumina, San Diego, Calif., USA) or NEBNext 33-MDS gene panel (New England Biolabs, Ipswich, Mass., USA).

FIG. 4 shows the effect of different combinations of sulforaphane, resveratrol and curcumin on OCI-M2 AZA-S [Sensitive] with addition of AZA.

FIG. 5 shows the effect of different combinations of sulforaphane, resveratrol and curcumin on OCI-M2 AZA-R #1 [Resistant] with addition of AZA. Said figure shows that the combination of all three plant derived compounds sulforaphane, resveratrol and curcumin when employed together with azacitidine was able to successfully decrease/reverse the AZA resistance in AZA-R cells. Particularly, at lower dosages of AZA, said combination of all three plant derived compounds showed better cytotoxicity than a combination of only two of the plant derived compounds (eg. resveratrol and sulforaphane, or sulforaphane and curcumin) with AZA, thereby indicating successful reversal of azacitidine resistance.

Thus, the results of FIGS. 4 and 5 demonstrate that the combination of all three plant derived compounds sulforaphane, resveratrol and curcumin together with azacitidine lead to higher cytotoxicity in both OCI-M2 AZA-S and OCI-M2 AZA-R cells. On the other hand, when azacitidine was provided along with only sulforaphane or a combination of only two of the plant derived compounds (eg. resveratrol and sulforaphane, or sulforaphane and curcumin), the cytotoxicity was lower than employing the combination of all three plant derived compounds sulforaphane, resveratrol and curcumin together with azacitidine. Said results further showcase the improved technical effect of the presently described combination (i.e. sulforaphane, resveratrol and curcumin+a hypomethylating agent such as azacitidine) and also the fact that said effect is not a simple sum of effects of the three components, but is synergistic/unexpected since not any combination of the three plant derived compounds (eg. resveratrol and sulforaphane+azacitidine, or, sulforaphane and curcumin+azacitidine) lead to said effects.

More particularly, the reversal of AZA resistance in AZA-R cells and thereby re-sensitizing said cells to AZA by employing the combination of sulforaphane, resveratrol and curcumin with azacitidine is surprising. Hypomethylating agents such as AZA are known to inhibit DNA CpG methylation and one of the reasons for resistance is through GSH (glutathione) pathway. Each of these plant compounds/agents (sulforaphane, resveratrol and curcumin) impact albeit differently the metabolic pathways involving both GSH and ROS (reactive oxygen species), as well as the PI3K/AKT1 pro-survival pathway. In other words, GSH pathway is inhibited by the combination of Sulforaphane, Resveratrol and Curcumin, thereby re-sensitizing AZA-R cells.

Example 3: Effect of Sulforaphane, Resveratrol and Curcumin Treatment on OCI-M2 Across a Large Concentration Gradient Experiment was conducted to evaluate the extent by which sulforaphane [SUL], resveratrol [RES], and curcumin [CUR] affected cell viability. FIG. 6 shows the effect of individual sulforaphane, resveratrol and curcumin treatment on OCI-M2 AZA-S cells across a large concentration gradient (0.01 uM to 100 uM). AZA-S cells were not affected by SUL, RES and CUR across the large concentration gradient.

Example 4: Effect of Sulforaphane ISFN1, Resveratrol [RES] and Curcumin ICUR1 Treatment on OCI-M2 AZA-S Cells Followed by Addition of AZA at Different Concentrations Experiments were conducted to evaluate the extent by which sulforaphane [SFN], resveratrol [RES] and curcumin [CUR] individually affected cell viability in combination with azacitidine [AZA]. FIG. 7 shows the individual effects of sulforaphane, resveratrol and curcumin treatment (5 µL each) on OCI-M2 AZA-S cells followed by addition of AZA at different concentrations (0.01 uM to 100 uM). AZA-S cells when provided with sulforaphane [SFN], resveratrol [RES] and curcumin [CUR] individually were affected by addition of AZA at different concentrations. However, said effects of individual plant based ingredients sulforaphane, resveratrol and curcumin was far lower than the 2-ingredient or the 3-ingredient treatments (FIG. 4). Further, based on the results of FIGS. 4 and 7, it is clear that the cytotoxicity achieved was highest with the 3-ingredient treatment along with AZA in AZA-S cells i.e. cytotoxicity: 1-ingredient<2-ingredient<3-ingredient.

Example 5: Effect of Plant Derived Compounds Along with Azacitidine on OCI-M2 AZA-S and AZA-R Cells AZA-R cells when preincubated with sulforaphane [SFN] led to increase in efficacy of AZA, while preincubating the cells with resveratrol [RES] or curcumin [CUR] had negligible effect (data not shown). However, surprisingly, the triple combination of sulforaphane+resveratrol+curcumin displayed the highest increase in AZA-mediated cytotoxicity. Likewise, AZA-S cells also showed higher AZA-induced cytotoxicity when preincubated with the triple combination of sulforaphane+resveratrol+curcumin, although the cytotoxicity increase was slightly lower in comparison to AZA-R cells. FIG. 8 demonstrates the effect of sulforaphane vs. the combination of sulforaphane+resveratrol+curcumin treatment (5 µL each) on OCI-M2 AZA-S [Sensitive] cells followed by addition of AZA at different concentrations (0.01 µM to 100 µM). FIG. 9 demonstrates the effect of sulforaphane vs. the combination of sulforaphane+resveratrol+curcumin treatment (5 µL each) on OCI-M2-AZA-R [Resistant] cells followed by addition of AZA at different concentrations (0.01 µM to 100 µM).

The results of FIGS. 8 and 9 showcase that the combination of all three plant derived compounds sulforaphane, resveratrol and curcumin together with azacitidine lead to higher cytotoxicity in both OCI-M2 AZA-S and OCI-M2 AZA-R cells. More importantly, while resveratrol or curcumin or sulforaphane when individually combined with azacitidine had low/negligible effects on cytotoxicity in AZA-R cells, the combination of sulforaphane, resveratrol and curcumin together with azacitidine was able to reverse the resistance of azacitidine in said AZA-R cells (FIG. 9). Said results further showcase the improved technical effect of the presently described combination (i.e. sulforaphane, resveratrol and curcumin+a hypomethylating agent such as azacitidine) and also the fact that said effect is not a simple sum of effects of the three components, but is synergistic/unexpected since the three plant based components sulforaphane, resveratrol and curcumin when individually provided with azacitidine showed negligible/lesser effect in inducing cytotoxicity.

Example 6: Effect of AZA+SFN/CUR/RES on AZA-R Models of SKM1 and MOLM13

In order to further validate the above discussed results which are based on single MDS/AML OCI-M2 cell line, AZA-R cells from two additional MDS/AML cell lines (SKM1 and MOLM13) were generated. FIG. 10 shows the effect of combination of sulforaphane+resveratrol+curcumin treatment (5 µL each) on SKM1-R [Resistant] followed by addition of AZA at different concentrations (0.01 µM to 100 µM). FIG. 11 shows the effect of combination of sulforaphane+resveratrol+curcumin treatment (5 µL each) on MOLM13-R [Resistant] followed by addition of AZA at different concentrations (0.01 µM to 100 µM).

The effect of sulforaphane+resveratrol+curcumin preincubation prior to providing azacitidine was successfully validated in the two additional SKM1 and MOLM13 AZA-R models. The results indicated that $IC_{50}$ of azacitidine in AZA-R cells (SKM1 and MOLM13) treated with sulforaphane, resveratrol and curcumin markedly decreased to the levels significantly lower than that of AZA-R cells treated with azacitidine alone. For instance, in FIG. 10 (SKM1 cell-line), the black line (IC50=5.94) was compared with red line (IC50=0.64) which shows that the combination of sulforaphane, resveratrol and curcumin helps to overcome AZA resistance in SKM1 AZA-R cell-line. Similarly, in FIG. 11 (MOLM13 cell-line), the black line (IC50=2.36) was compared with red line (IC50=0.68) which shows that the combination of sulforaphane, resveratrol and curcumin helps to overcome AZA resistance in MOLM13 AZA-R cell-line.

Example 7: Additional Effect of Genomic Aberrations in Cancer Cells

While the present combination therapy disclosed herein can be employed in any patient suffering from MDS or AML, and works synergistically to improve the treatment as well as decreasing or overcoming drug resistance (eg. azacitidine or decitabine) in patients, a further understanding of the correlation of gene aberrations and the additional positive effect (if any) of sulforaphane, resveratrol and curcumin combination along with HMA (eg. azacitidine) was studied. AZA-R OCI-M2 cells and AZA-S OCI-M2 cells were generated as described the earlier examples and gene aberrations were analysed. Gene aberrations in three additional MDS/AML cell lines—SKM1, MOLM13 and K562 were also studied. The gene aberration status in different cell lines of MDS/AML is illustrated in Table 1 below.

TABLE 1

| | OCI-M2 cell line (AZA-S) | OCI-M2 cell line (AZA-R) | SKM-1 cell line | MOLM-13 cell line | K562 cell line |
|---|---|---|---|---|---|
| ASXL1 | ✓ | ✓ | ✓ | x | ✓ |
| TET2 | ✓ | ✓ | ✓ | x | x |
| RCS Sensitivity | ++++ | ++++ | +++ | + | +++ |

Based on the extensive analysis of aberrations in different cell lines (Table 1) and results of the corresponding effect of sulforaphane, resveratrol and curcumin combination with azacitidine said cell lines as shown in FIG. 19, it was found that while all the tested cell types were already very effective in increasing cytotoxicity based on the sulforaphane, resveratrol and curcumin combination along with azacitidine, the cytotoxicity effect was found to be even more profound in AZA-R OCI-M2 cells, AZA-S OCI-M2 cells and SKM1 cells possessing mutations in TET2 and/or ASXL1. These results therefore additionally show that the efficacy of the presently described combination of sulforaphane, resveratrol and curcumin along with azacitidine in treating MDS/AML can be further enhanced in the presence of genomic aberration(s) in at least one gene selected from tet methylcytosine dioxygenase 2 (TET2) and ASXL transcriptional regulator 1 (ASXL1).

Example 8: Effect of GSH Inhibitor on AZA-S and AZA-R Cells

To investigate whether GSH (an ultimate target of SFN, CUR and RES actions) is directly involved in the AZA resistance, DL-buthionine-sulfoximine (BSO, Sigma) that is known to reduce levels of GSH by inhibiting gamma-glutamyl cysteine synthetase (GCL) was utilized. The extent by which BSO-mediated depletion of GSH affected AZA cytotoxicity was tested by using WST-1 assay at different concentrations of AZA (0.01 µM to 100 µM) for about 72 hours.

FIG. 12 shows the effect of DL-buthionine-sulfoximine (BSO) [GSH Inhibitor] treatment on cytotoxicity of AZA in a dose-dependent manner. It was observed that BSO treatment of AZA-R cells resulted in higher cytotoxicity of AZA in a dose-dependent manner. The effect of BSO was similar to the effect of sulforaphane+resveratrol+curcumin preincubation which implicates that GSH pathway serves an important role as common mediator of AZA resistance, and also re-establishes the criticality of sulforaphane+resveratrol+curcumin in overcoming AZA resistance in addition to achieving improved cytotoxicity.

Example 9: Effect of the Combination of Sulforaphane, Resveratrol and Curcumin Along with Azacitidine in CDX-MDS Mice A mouse model was established based on AZA-S or AZA-R cells, wherein said cells were intraosseally injected into immunodeficient mice strain called NSGS mice expressing human cytokines IL-3, GM-CSF and SCF. Cells were lentivirally transduced to express luciferase for in vivo imaging thus producing a Cell-line Derived Xenograft (CDX) model.

Initially, it was tested whether the mice CDX models based on AZA-S or AZA-R cells have differential response to AZA. Following seven i.p. injections of AZA (Vidaza, Celgene) at a dose of 150 µg/mouse, a significant prolongation of survival in AZA-S CDX mice was achieved but not in AZA-R CDX mice. The AZA dose and therapeutic regimen were similar to the dosing used in humans and was based on a previously determined AZA toxicity study for this particular mouse strain.

To determine the extent by which the combination of sulforaphane, resveratrol and curcumin sensitized AZA-R disease to AZA, AZA-R cells were transplanted into CDX mice and the mice was treated with either AZA alone or AZA in combination with sulforaphane [SFN], resveratrol [RES] and curcumin [CUR] 3 times a week. For each mouse, a mixture of SFN, RES and CUR comprising 25 µg of each of SFN, RES and CUR dissolved in a vehicle containing 5% DMSO, 30% PEG300 and PBS (phosphate buffered saline) was used. Said mixture was administered intraperitoneally immediately after mixing and was employed concurrently with AZA application. As expected from in vitro data, AZA-R CDX mice treated with AZA and the combination of sulforaphane, resveratrol and curcumin achieved an increase in both event free and overall survival compared to the AZA alone arm. Taken together, these results provided successful evidence that modulating GSH/ROS levels with the redox-modifiers (RES, CUR and SFN) lead to enhanced AZA efficacy in vivo using an experimental CDX model. More importantly, said results also demonstrate the decrease or reversal of AZA resistance when a therapeutic effective amount of a combination of sulforaphane, resveratrol and curcumin along with a therapeutic effective amount of AZA is administered in vivo.

FIG. 13 depicts in vivo imaging of (A) AZA-S and (B) AZA-R cell lines transfected Cell-line Derived Xenograft (CDX) mice models. The mice xenotransplanted with AZA-R cell line treated with AZA display shorter OS compared to mice treated with combination of SFN+RES+CUR and AZA (43 vs. 57 days, p value=0.038). The mice xenotransplanted with AZA-R cell line treated with AZA displayed poorer EFS compared to mice treated with the combination of SFN+RES+CUR and AZA (28 vs. 46 days, p value=0.032). FIG. 14 shows OS [Overall Survival] curve for mice xeno-transplanted with AZA-R cell line treated with AZA compared to mice treated with combination of SFN+RES+CUR and AZA. FIG. 15 shows EFS [Event Free Survival] curve for mice xeno-transplanted with AZA-R cell line treated with AZA compared to mice treated with combination of SFN+RES+CUR and AZA.

Example 10: Clinical Study in High-Risk MDS/AML Patients Involving Administration of Sulforaphane, Resveratrol and Curcumin Along with Standard Chemotherapy (Hypomethylating Agent)

Clinical study was conducted in high-risk MDS/AML human patients (patient IDs: CRS001 to CRS010) who underwent chemotherapy with azacitidine along with administration of the combination of Sulforaphane, Resveratrol and Curcumin. Tablets or capsules containing Sulforaphane, Resveratrol and Curcumin along with excipients such as calcium palmitate, silica, calcium ascorbate, rice flour, gelatin and hydroxypropyl methylcellulose were orally administered. Sulforaphane at 30 mg/d, Resveratrol at 250 mg/d, and Curcumin at 250 mg/d was employed in this study. As observed from FIG. 16, post administration of the combination of Sulforaphane, Resveratrol and Curcumin, many patients (eg. CRS004, CRS009, CRS006 and CRS003) achieved remission i.e. a decrease in or disappearance of signs and symptoms of MDS/AML which was either a partial remission (disappearance of some, but not all, signs and symptoms of MDS/AML) or a complete remission (disappearance of all signs and symptoms of MDS/AML although MDS/AML still may be in the body). Additionally, patient CRS004 acquired resistance during azacitidine treatment and the MDL/AML had progressed significantly. However, surprisingly, upon administration of the Sulforaphane, Resveratrol and Curcumin combination, said patient CRS004 showed improvement by reversing the azacitidine resistance and achieved remission. Further details on the case study of patient CRS004 is depicted in FIG. 17. These results show that the combination therapy (combination of Sulforaphane, Resveratrol and Curcumin+azacitidine) described herein had a positive impact on reversal of azacitidine resistance in addition to achieving improved treatment of MDL/AML.

Further, as indicated in FIG. 18, no significant difference in whole blood cell levels or in selected set of biochemical tests were observed in patients when administered the combination therapy as described herein. Also, no myelo, hepato or renal toxicity was observed, and there were no signs of tumor lysis syndrome.

Example 11: Effect of Plant Derived Compounds Along with Decitabine in Overcoming Decitabine Resistance The effect of the combination of resveratrol, curcumin and sulforaphane was tested for overcoming decitabine resistance.

The above discussed experiments/examples had established the fact that CRS (curcumin, resveratrol and sulforaphane) overcomes AZA resistance in MDS/AML cells OCIM2, SKM1 and MOLM-13-AZA-S and AZA-R cells [model of acquired resistance achieved using high dose of AZA]. FIG. 20A, B, D, E, F and Table 2 further illustrate that in the same OCIM2 (AZA-S and AZA-R), SKM1 (AZA-S) and MOLM-13 (AZA-S and AZA-R) cell models, treatment with decitabine and CRS improved the outcome (i.e. achieved higher cytotoxicity and lower cell viability) compared to treatment with decitabine alone [Note: AZA-S and AZA-R OCIM2, SKM1 and MOLM-13 cell-lines are not resistant to decitabine].

Now, to further understand the effects in decitabine (DEC) resistant cells, experiments were conducted with a DEC resistant cell-line—K562. FIG. 20C and Table 2 illustrates the experimental results in K562 cell line (cells resistant to decitabine). Said results surprisingly show that the combination of CRS (curcumin, resveratrol and sulforaphane) overcomes this decitabine (DEC) resistance in decitabine resistant K562 cells—see IC50 of 1.495 with decitabine alone treatment vs. IC50 of 0.18 with CRS and decitabine treatment. The results also show that the effect of BSO (GSH inhibitor) was similar to the effect of curcumin+resveratrol+sulforaphane implicating that GSH pathway serves an important role as common mediator of decitabine resistance, and also re-establishes the criticality of curcumin+resveratrol+sulforaphane in overcoming decitabine resistance in addition to achieving improved cytotoxicity.

TABLE 2

| Cell Line - IC50 (µM) | Decitabine | Decitabine + CRS | Decitabine + BSO | % Change of IC50 in Cell Line (Decitabine + CRS vs. Decitabine) |
|---|---|---|---|---|
| OCI-M2 (AZA-S) | 0.02947 | 0.01134 | 0.01689 | 62% |
| OCI-M2 (AZA-R) | 0.04765 | 0.01793 | 0.03367 | 62% |
| K562 | 1.495 | 0.187 | 0.0831 | 87% |
| SKM1 (AZA-S) | 0.7443 | 0.3691 | 0.4760 | 50% |
| MOLM-13 (AZA-S) | 0.04670 | 0.01457 | 0.04599 | 69% |
| MOLM-13 (AZA-R) | 0.08207 | 0.01321 | 0.06894 | 84% |

Conclusion

Overall, it was observed that dysregulation of GSH/ROS metabolism is a central mechanism of azacitidine (AZA) and decitabine (DEC) resistance. The combination of resveratrol, curcumin and sulforaphane was able to re-sensitize AZA-resistant cells to AZA treatment and DEC-resistant cells to DEC treatment in vitro. In vivo experiments using experimental mouse model and clinical evidence in MDL/AML human patients are also provided which shows that treating MDS/AML with the combination of resveratrol, curcumin and sulforaphane enhanced the AZA efficacy. Taken together, the present results/observations provide successful evidence that resveratrol, curcumin and sulforaphane when combined with a hypomethylation agents AZA or DEC unexpectedly leads to an enhanced AZA or DEC efficacy in treating MDL or AML. Additionally, said results also demonstrate that resveratrol, curcumin and sulforaphane when combined with hypomethylation agent azacitidine (AZA) or decitabine (DEC) reverses AZA or DEC resistance in a patient, thereby making the patient sensitive/responsive to AZA or DEC treatment.

Example 12: Observational Study of the Effects of Phytocannabinoids on Quality of Life of Patients Undergoing MDS/AML Treatment Using Hypomethylating Agent (HMA)

A broad spectrum plant extract of targeted biologically active compounds comprising cannabidiol (CBD), cannabigerol (CBG), cannabinol (CBN), cannabidivarin (CBDV), cannabichromene (CBC) and tetrahydrocannabivarin (THCV) was obtained from *Cannabis Sativa* L. using the method described in U.S. Pat. No. 10,507,407 B2. The extracted plant material was then adjusted for higher biological availability by mixing with cocoa butter as a carrier and encapsulated in hydroxypropyl methylcellulose (HPMC) capsules at a concentration of 60 mg of extract per capsule and 500 mg of the carrier for the purpose of oral administration. One capsule per day was administered to the patients. In an observational study of the effect of phytocannabinoids on quality of life when administered in patients undergoing treatment for hematological malignancies using hypomethylating agent (HMA), it was seen that 72% of the responders undergoing HMA treatment experienced significantly reduced side effects such as nausea, vomiting, decreased appetite, pain, muscle cramps, insomnia, anxiety and depression.

Example 13: Observational Study of the Effects of Topical Administration of Phytocannabinoids to the Area/Site of Hypomethylating Agent (HMA) Administration A broad spectrum plant extract of targeted biologically active compounds comprising cannabidiol (CBD), cannabigerol (CBG), cannabinol (CBN), cannabidivarin (CBDV), cannabichromene (CBC) and tetrahydrocannabivarin (THCV) was obtained from *Cannabis Sativa* L. using the method described in U.S. Pat. No. 10,507,407 B2. The extracted material was then adjusted for higher local and transdermal biological availability by mixing with pharmaceutical vaseline as a carrier at a total concentration of 1% of the extract for the purpose of topical administration. The mixture was applied at the site of the subcutaneous application of the hypomethylating agent (HMA) immediately after HMA administration. In an observational study of the effect of phytocannabinoids on quality of life when administered in patients undergoing treatment for hematological malignancies using hypomethylating agent (HMA), it was seen that 66% of the responders undergoing HMA treatment experienced significantly reduced side effects such as injection site granuloma, tissue inflammation, skin lesion, skin rash and itching at injection site.

The invention claimed is:

1. A method for decreasing resistance to a hypomethylating agent caused by treatment of hematological malignancy in a subject in need thereof, which comprises administering a therapeutically effective amount of a combination comprising sulforaphane, resveratrol, and curcumin to the subject,
   wherein the hypomethylating agent is azacitidine, decitabine, or a combination thereof,
   and wherein the hematological malignancy is myelodysplastic syndrome or acute myeloid leukemia.

2. The method as claimed in claim 1, wherein the subject has already been administered, or is undergoing treatment with, a therapeutically effective amount of the hypomethylating agent.

3. The method as claimed in claim 1, wherein decreasing resistance to a hypomethylating agent comprises improving sensitivity of the subject to the hypomethylating agent during treatment of the hematological malignancy as compared to administration of the hypomethylating agent prior to administering the combination.

4. A method of treating a hematological malignancy selected from myelodysplastic syndrome and acute myeloid leukemia in a subject in need thereof, which comprises administering:
   a) a therapeutically effective amount of a combination comprising sulforaphane, resveratrol, and curcumin; and
   b) a therapeutically effective amount of hypomethylating agent selected from azacitidine, decitabine, and a combination thereof, to the subject.

5. The method as claimed in claim 4, wherein a) and b) are administered concurrently, sequentially, or at different time intervals.

6. The method as claimed in claim 4, wherein the subject has already been administered, or is already undergoing the treatment with, a therapeutically effective amount of the hypomethylating agent.

7. The method as claimed in claim 4, wherein the method has an enhanced therapeutic effect in the treatment of hematological malignancy compared to the effect of hypomethylating agent when administered alone; or the method improves sensitivity of the subject to the hypomethylating agent during treatment of the hematological malignancy.

8. The method as claimed in claim 1, wherein the combination comprising sulforaphane, resveratrol and curcumin is:
   i. a single formulation of sulforaphane, resveratrol, curcumin, and a pharmaceutically acceptable excipient; or
   ii. separate formulations of:
      I. sulforaphane and a pharmaceutically acceptable excipient,
      II. resveratrol and a pharmaceutically acceptable excipient, and
      III. curcumin and a pharmaceutically acceptable excipient.

9. The method as claimed in claim 1, wherein the hypomethylating agent is administered as a formulation comprising the hypomethylating agent and a pharmaceutically acceptable excipient.

10. The method as claimed in claim 8, wherein the pharmaceutically acceptable excipient is chosen from a carrier, a binder, an encapsulant, a coating, a color, a preservative, a lubricant, a disintegrant, saline, a gelling agent, and combinations thereof.

11. The method as claimed in claim 9, wherein the pharmaceutically acceptable excipient is chosen from a carrier, a binder, an encapsulant, a coating, a color, a preservative, a lubricant, a disintegrant, saline, a gelling agent, and combinations thereof.

12. The method as claimed in claim 1, wherein the hematological malignancy or the resistance to hypomethylating agent is caused by genomic aberration in at least one gene selected from tet methylcytosine dioxygenase 2, ASXL transcriptional regulator 1, and a combination thereof.

13. The method as claimed in claim 1, wherein sulforaphane, resveratrol, and curcumin are derived from plants.

14. The method as claimed in claim 1, wherein the combination comprising sulforaphane, resveratrol, and curcumin is administered at a therapeutically effective amount ranging from about 0.05 mg/kg body weight to 10 mg/kg body weight; or the hypomethylating agent is administered at a therapeutically effective amount ranging from about 0.2 mg/kg body to 12 mg/kg body.

15. The method as claimed in claim 1, wherein the combination comprising sulforaphane, resveratrol, and curcumin is administered orally, intravenously, intramuscularly, subcutaneously, intraosseally, topically, or any combination thereof or the hypomethylating agent is administered orally, intravenously, intramuscularly, subcutaneously, intraosseally, topically, or any combination thereof.

16. The method as claimed in claim 1, wherein the subject is a mammal.

17. The method as claimed in claim 1, wherein the subject is a human who has developed resistance to treatment with hypomethylating agent, or a human who is sensitive to treatment with hypomethylating agent.

18. A pharmaceutical kit or package comprising:
   a) a therapeutically effective amount of a combination essentially consisting of sulforaphane, resveratrol, and curcumin;
   b) optionally, a therapeutically effective amount of hypomethylating agent selected from azacitidine, decitabine, or a combination thereof;
   c) optionally, a therapeutically effective amount of at least one of cannabidiol, cannabigerol, cannabinol, cannabidivarin, cannabichromene, tetrahydrocannabivarin, or any combination thereof; and d) an instruction manual containing instructions for using a), b) and c).

19. The pharmaceutical kit or package as claimed in claim 18, wherein the pharmaceutical kit or package is used in the treatment of hematological malignancy or for decreasing resistance to the hypomethylating agent caused by treatment of hematological malignancy, in a subject in need thereof,
and wherein the hematological malignancy is myelodysplastic syndrome or acute myeloid leukemia.

20. The method as claimed in claim 1, further comprises oral administration of a therapeutically effective amount of at least one of cannabidiol, cannabigerol, cannabinol, cannabidivarin, cannabichromene, tetrahydrocannabivarin, or any combination thereof, to reduce side effects of the hypomethylating agent;
or topical administration of a therapeutically effective amount of at least one of cannabidiol, cannabigerol, cannabinol, cannabidivarin, cannabichromene, tetrahydrocannabivarin, or any combination thereof, to the area of subcutaneous administration of the hypomethylating agent to reduce its side effects.

* * * * *